United States Patent
Nguyen et al.

(10) Patent No.: US 12,118,723 B1
(45) Date of Patent: Oct. 15, 2024

(54) COMPUTE SYSTEM WITH IMAGE BASED SKIN CANCER DETECTION MECHANISM AND METHOD OF OPERATION THEREOF

(71) Applicant: BelleTorus Corporation, Cambridge, MA (US)

(72) Inventors: Thi Thu Hang Nguyen, Toulouse (FR); Tien Dung Nguyen, Toulouse (FR); Thanh Thi Nguyen, Toulouse (FR); Jean-Luc Perrot, Saint-Etienne (FR); Jonathan Wolfe, Plymouth Meeting, PA (US)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/423,874

(22) Filed: Jan. 26, 2024

Related U.S. Application Data

(60) Provisional application No. 63/509,372, filed on Jun. 21, 2023.

(51) Int. Cl.
*G06T 7/00* (2017.01)
*G06V 10/764* (2022.01)
(Continued)

(52) U.S. Cl.
CPC .......... *G06T 7/0012* (2013.01); *G06V 10/764* (2022.01); *G16H 30/40* (2018.01);
(Continued)

(58) Field of Classification Search
CPC ......... G06T 7/0012; G06T 2207/30088; G06T 2207/30096; G06T 2207/20081; G06T 2207/20084; G06T 2207/10024; G06T 7/90; G06T 2207/20132; G06T 2207/10004; G06T 2207/10056; G06T 7/11; G06T 7/12; G06T 3/4046;
(Continued)

(56) References Cited

U.S. PATENT DOCUMENTS

| | | | |
|---|---|---|---|
| 2008/0226151 A1* | 9/2008 | Zouridakis | G06T 7/0012 600/300 |
| 2022/0133215 A1* | 5/2022 | Mayer | G16H 30/40 600/477 |

FOREIGN PATENT DOCUMENTS

WO   WO-2019091509 A1 *   5/2019

OTHER PUBLICATIONS

Machine translation of WO-2019091509-A1 obtained from google patents (Year: 2019).*

(Continued)

*Primary Examiner* — Aaron W Carter
*Assistant Examiner* — Courtney Joan Nelson
(74) *Attorney, Agent, or Firm* — Perspectives Law Group, Corp.

(57) ABSTRACT

A method of operation of a compute system includes: receiving a patient image; segmenting a skin lesion in the patient image; constructing a normalized image by cropping the patient image and adding padding to position the skin lesion at the center of the normalized image; identifying, by a cancer artificial intelligence (AI) already trained, a skin cancer classification, a skin cancer sub-class, and a risk level assessment; and generating a skin cancer display including the normalized image, the skin cancer classification, the skin cancer sub-class, and the risk level assessment for displaying on a device.

20 Claims, 15 Drawing Sheets
(12 of 15 Drawing Sheet(s) Filed in Color)

(51) Int. Cl.
*G16H 30/40* (2018.01)
*G16H 50/20* (2018.01)

(52) U.S. Cl.
CPC ... *G16H 50/20* (2018.01); *G06T 2207/20132* (2013.01); *G06T 2207/30088* (2013.01); *G06T 2207/30096* (2013.01)

(58) Field of Classification Search
CPC ... G06T 7/13; G06T 2207/30004; G06T 7/10; G06N 3/08; G06N 20/00; G06N 3/02; G06N 3/0464; G06V 10/82; G06V 2201/03; G06V 10/56; G06V 10/25; G06V 20/698; G06V 10/764; A61B 5/444; A61B 5/441; A61B 5/445; A61B 5/7264; A61B 5/7267; A61B 5/0033; A61B 2576/00; G16H 50/20; G16H 30/40; G16H 50/30; G16H 30/20; G06F 18/2431; G06F 18/21; G06F 18/254
See application file for complete search history.

(56) References Cited

OTHER PUBLICATIONS

E. Vocaturo, D. Perna and E. Zumpano, "Machine Learning Techniques for Automated Melanoma Detection," 2019 IEEE International Conference on Bioinformatics and Biomedicine (BIBM), San Diego, CA, USA, 2019, pp. 2310-2317, doi: 10.1109/BIBM47256. 2019.8983165 (Year: 2019).*

* cited by examiner

COMPUTE SYSTEM WITH IMAGE BASED SKIN CANCER DETECTION MECHANISM AND METHOD OF OPERATION THEREOF

CROSS-REFERENCE TO RELATED APPLICATION(S)

This application claims the benefit of U.S. Provisional Patent Application Ser. No. 63/509,372 filed Jun. 21, 2023, and the subject matter thereof is incorporated herein by reference thereto.

TECHNICAL FIELD

An embodiment of the present invention relates generally to a compute system, and more particularly to a system with an image based skin cancer detection mechanism.

BACKGROUND

Cancer of skin is common worldwide, it is even the most common cancer in Australia and New Zealand. Non-melanoma cancer of skin represents in 2020, approximately 1.2 million new cancer (6.2% of total new cancer worldwide) and 63 thousands cancer death (0.6% of all cancer death). On the other hand, melanoma represents 324 thousands new cancer and almost the same amount of death: 57 thousands cancer death (0.6% of all cancer death). Prevention with sunscreen, and early detection for better treatment are key in order to reduce mortality.

Thus, a need still remains for a compute system with an image based skin cancer detection mechanism to provide an objective analysis of skin abnormalities and cancer detection at an earlier stage of development. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: receiving a patient image; segmenting a skin lesion in the patient image; constructing a normalized image by cropping the patient image and adding padding to position the skin lesion at the center of the normalized image; identifying, by a cancer artificial intelligence (AI) already trained, a skin cancer classification, a skin cancer sub-class, and a risk level assessment; and generating a skin cancer display including the normalized image, the skin cancer classification, the skin cancer sub-class, and the risk level assessment for displaying on a device.

An embodiment of the present invention provides a compute system, including a control circuit, including a processor, configured to: receive a patient image; segment a skin lesion in the patient image; construct a normalized image by cropping the patient image and adding padding to position the skin lesion at the center of the normalized image; identify, by a cancer artificial intelligence (AI) already trained, a skin cancer classification, a skin cancer sub-class, and a risk level assessment; and generate a skin cancer display including the normalized image, the skin cancer classification, the skin cancer sub-class, and the risk level assessment for displaying on a device.

An embodiment of the present invention provides a non-transitory computer readable medium including instructions for a compute system, including: receiving a patient image; segmenting a skin lesion in the patient image; constructing a normalized image by cropping the patient image and adding padding to position the skin lesion at the center of the normalized image; identifying, by a cancer artificial intelligence (AI) already trained, a skin cancer classification, a skin cancer sub-class, and a risk level assessment; and generating a skin cancer display including the normalized image, the skin cancer classification, the skin cancer sub-class, and the risk level assessment for displaying on a device.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
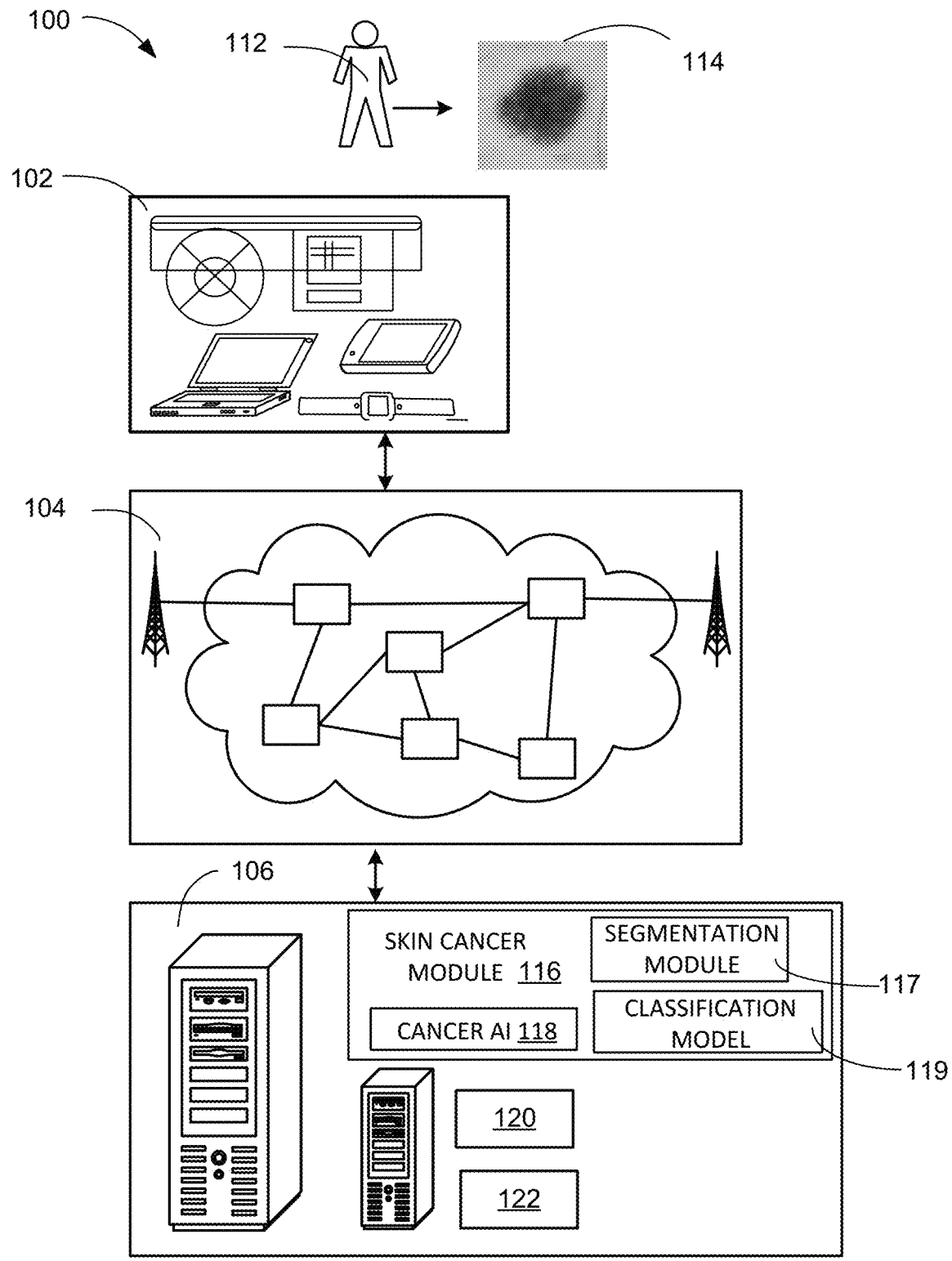
FIG. 1 is an example of a system architecture diagram of a compute system with an image based skin cancer detection mechanism in an embodiment of the present invention.

Embodiments can detect not only 10 different classes of skin cancer including Melanoma (MEL), Basal Cell Carcinoma (BCC), Epidermal tumors (EPI), Malignant lesions (MALO), Melanocytic Nevus (NV), Dermatofibroma (DF), Benign Adnexal Lesions (BAL), Benign Keratinocytic Lesions (BKL), Benign Vascular lesions (VASC) and Benign Lesions (BENO) but also 122 other subtypes for example Melanoma in situ, Melanoma nodular, etc. Example of embodiments use hierarchical learning (class and sub-class) which gives more accurate result then training with class information only. As an example, embodiments can include two steps: lesion segmentation and lesion classification. With this type of learning, each lesion has two label, one for class and the other for sub-class (or sub-type). If a lesion does not have sub-type information, we will set the gradient be zero so that it will not affect the back-propagation process. Embodiments underwent a blind test using a test set of 4926 images and we got an average of 0.95 of AUC (area under the curve) and 0.94 for MEL, 0.97 for NV, and 0.98 for BCC.

Embodiments improve upon automatic detection of skin cancer with image analysis, especially with the use of deep learning. AI models gives more accurate prediction than doctors. A convolutional neural network (CNN) can be trained with over four thousand dermatoscopic images that are biopsy-proven of melanoma and nevi (half-half split). Then compare the result of the CNN on 800 more similar pictures (not from the dataset), with the majority result of dermatologists taken from nine German university hospitals. The CNN had higher sensitivity, 82.3% instead of 67.2%, and higher specificity 77.9% instead of 62.2%, with disjoint 95% confidence interval. Using AI in skin cancer detection is not to replace doctors but to help them. The CNN might help the diagnosis, as the misdiagnosed melanoma are different for expert and CNN. Similarly, giving the result of an AI model to dermatologists, as a second opinion, can improve the diagnostic quality. In the trained CNN, an AI can suggest to do an excision of the lesion, a clinical follow up, or to do nothing.

Embodiments can perform subclass-based training technique for deep neural networks (DNN) that lead to an improvement in both robustness and accuracy. The criterion of the embodiment for identifying the neglected classes are input during the training. An embodiment also proposed to split the neglected classes into subclasses using a clustering method and apply a new loss function using subclass partitions. The embodiment resulted in a DNN with higher overall generalization performance on several benchmarks datasets for multiclass and multilabel classification. An embodiment has trained a model to split each class into estimated subclasses via unsupervised clustering in the model's feature space. These estimated subclass labels are then used during the training of the classification model. The resulting model is more robust and has a significantly higher worst-case subclass accuracy on several real-world and benchmark image classification datasets including ISIC challenge 2020.

Example of embodiments, can be referred to as Skin Cancer AI, using hierarchical learning. Embodiments generate a very detailed classification system that contains 10 classes and 122 sub-classes, in which a class might have up to 16 sub-classes. Embodiments do not estimate the subclass labels using clustering method, but rather set the gradient be zero so that missing subclass will not affect the learning process.

Embodiments of the skin cancer classification system. Skin cancer detection itself is a very complex classification problem since there are thousands of lesion types which have been known. Besides, the famous mimickers, such as melanoma and nevus, make it extremely hard to distinguish between benign and malignant lesions. To tackle a such difficult classification problem, it is crucial to have a good classification system. Embodiments address some serious weakness of classification system. Embodiments addressed these weaknesses with a new classification system which is much more detailed with 10 classes and 122 sub-classes. Hereafter embodiments implement the discoveries into classification system.

An ISIC classification system for skin cancer detection contains nine classes: melanoma (MEL), melanocytic nevus (NV), basal cell carcinoma (BCC), actinic keratosis (AK), benign keratosis including solar lentigo, seborrheic keratosis and lichen planus-like keratosis (BKL), dermatofibroma (DF), vascular lesion (VASC), squamous cell carcinoma (SCC), and unknown (UNK). This system covers the most common malignant and benign classes of skin lesions. It is easy for doctors to annotate, and also more informative than the binary classification "malignant vs benign". However, the ISIC classification system has some serious weaknesses that will be explain hereafter.

Firstly, the ISIC classification system is ambiguous and not backward-compatible. Many skin lesions are difficult to classify into one of the nine given classes properly. For example, clear cell acanthoma and porokeratosis are benign keratinocytic lesions, but they are not included in the BKL class by ISIC's definition. Another example is Bowen disease lesion which was included in AKIEC, together with AK, in ISIC challenge 2018. However, in ISIC challenge 2019, Bowen disease lesion is included in SCC and not AK class.

Secondly, many uncommon but important types of skin lesions, both benign and malignant, are missing in the classification. Examples include Merkel cell carcinoma, kaposi sarcoma, dermatofibrosarcoma protuberans, sebaceous gland hyperplasia, etc. These lesions all become unknown (UNK) in the ISIC classification system, and therefore, the trained model cannot recognize them in real life application.

Finally, the ISIC classification system does not provide enough information for determining the cancer risk level of skin lesions since lesions in the same class may have very different cancer risk levels. For example, pyogenic granuloma and cherry angioma are both in VASC class. However, pyogenic granuloma must have much higher cancer risk level because it looks very similar to other malignant lesions such as amelanotic melanoma and kaposi sarcoma. Similarly, Spitz nevus and dysplastic nevus look very similar to melanoma hence they must have much higher cancer risk level compared with other benign nevi.

Experiment setting participant: 3 doctors (Labeille, Chlod, Ravni) vs AI (Skin Cancer AI eta version) total 980 images of 245 unique lesions taken from 4 dermoscopes: FotoFinder, Visiomed, HorusX30, HorusX20 Doctor's answer Hypothesis/Dx: 'AK', 'BCC', 'Cyst', 'Lentigo', 'MEL', 'MEL_LM', 'MEL_Meta', 'NV', 'NV_Atyp', 'NV_Spitz', 'PAGET', 'SCC', 'SK', dunno Nature: malignant, benign, dunno Treatment/Modality: return to GP (return), monitor 3 months (M3), biopsy, excision Note: There are 2 tumors (BOFA & JOUJO3) where 4 images are not of the same lesion. Therefore, the 8 corresponding images are removed from the sheet, result in a total of 972 images and 243 lesions.

Here is the summary of 972 images by type and nature.

| Type | Images | Lesions | #Benign | #Malignant |
|---|---|---|---|---|
| AK | 16 | 4 | 16 | 0 |
| BCC | 252 | 63 | 0 | 252 |
| Cyst | 8 | 2 | 8 | 0 |
| Lentigo | 24 | 6 | 24 | 0 |
| MEL | 272 | 68 | 0 | 272 |
| MEL_LM | 76 | 19 | 0 | 76 |
| MEL_Meta | 12 | 3 | 0 | 12 |
| NV | 196 | 49 | 196 | 0 |
| NV_Atyp | 32 | 8 | 32 | 0 |
| NV_Spitz | 8 | 2 | 8 | 0 |
| Paget | 4 | 1 | 0 | 4 |
| SCC | 40 | 10 | 0 | 40 |
| SK | 32 | 8 | 32 | 0 |
| Sum | 972 | 243 | 316 | 656 |

Statistical study objectives

Principal objective: reproducibility of the dermatologist's diagnosis.

Secondary objectives:
  Reproducibility of AI's diagnosis
    Accuracy of dermatologists and AI on nature (benign/malignant) of the lesions, and diagnosis hypothesis, according to separate utilization or combined utilization of dermatoscope.
    Improvement of accuracy when combined versus separate utilization of dermatoscopes.

Statistics

Reproducibility of Dermatologist's & AI's Diagnosis

Main question: Does the dermatologist perform the same when using different dermoscope?

Analysis: agreement in dx hypothesis/nature/treatment when using different dermoscope.

Metrics: kappa (Cohen's Kappa when there are 2 raters, Fleiss' Kappa when there are more than 2 raters)

Cohen's kappa coefficient (x, lowercase Greek kappa) is a statistic that is used to measure inter-rater reliability (and also intra-rater reliability) for qualitative (categorical) items. It is generally thought to be a more robust measure than simple percent agreement calculation, as c takes into account the possibility of the agreement occurring by chance. There is controversy surrounding Cohen's kappa due to the difficulty in interpreting indices of agreement. Some researchers have suggested that it is conceptually simpler to evaluate disagreement between items.

Fleiss' Kappa is a statistical measure for assessing the reliability of agreement between a fixed number of raters when assigning categorical ratings to a number of items or classifying items. This contrasts with other kappas such as Cohen's kappa, which only work when assessing the agreement between not more than two raters or the intra-rater reliability (for one appraiser versus themselves). The measure calculates the degree of agreement in classification over that which would be expected by chance.

Fleiss' kappa works for any number of raters giving categorical ratings, to a fixed number of items, at the condition that for each item raters are randomly sampled. It can be interpreted as expressing the extent to which the observed amount of agreement among raters exceeds what would be expected if all raters made their ratings completely randomly. It is important to note that whereas Cohen's kappa assumes the same two raters have rated a set of items, Fleiss' kappa specifically allows that although there are a fixed number of raters (e.g., three), different items may be rated by different individuals. That is, Item 1 is rated by Raters A, B, and C; but Item 2 could be rated by Raters D, E, and F. The condition of random sampling among raters makes Fleiss' kappa not suited for cases where all raters rate all patients.

kappa interpretation:

| Kappa | Interpretation |
|---|---|
| <0 | No agreement |
| 0.0-0.20 | Slight agreement |
| 0.21-0.40 | Fair agreement |
| 0.41-0.60 | Moderate agreement |
| 0.61-0.80 | Substantial agreement |
| 0.81-1.00 | Almost perfect agreement |

Agreement in diagnosis hypothesis kappa is computed under assumption that
NV=NV_Atyp=NV_Spitz
MEL=MEL_LM=MEL_Meta 95& confidence level (CI) is computed using bootstrap sampling with 1000 repetitions. The following table indicates the relative capabilities of three clinicians versus the cancer AI with input from various medical image capture devices.

| | kappa | Dr. Labeille | Dr. Chloé | Dr. Ravni | CANCER AI |
|---|---|---|---|---|---|
| Cohen's kappa | FF vs Visiomed | 0.404-0.556 | 0.407-0.549 | 0.406-0.566 | 0.749-0.869 |
| | FF vs HorusX30 | 0.373-0.523 | 0.336-0.476 | 0.305-0.469 | 0.684-0.816 |
| | FF vs HorusX20 | 0.368-0.525 | 0.337-0.471 | 0.321-0.486 | 0.656-0.792 |
| | Visiomed vs HorusX30 | 0.387-0.541 | 0.359-0.506 | 0.334-0.505 | 0.629-0.771 |
| | Visiomed vs HorusX20 | 0.435-0.590 | 0.403-0.546 | 0.360-0.536 | 0.650-0.785 |
| | HorusX30 vs HorusX20 | 0.450-0.605 | 0.405-0.548 | 0.369-0.545 | 0.710-0.836 |
| Fleiss' kappa | Global | 0.426-0.527 | 0.395-0.493 | 0.372-0.487 | 0.696-0.796 |

Remarks:
  dermatologists have moderate agreement when using different dermoscopes while AI has substantial agreement.
  95% CI of cancer AI is separated from that of dermatologists=>cancer AI's kappa coefficient is statistically higher than that of dermatologists
  huge overlap of 95% CI between dermatologists=>difference in kappa coefficient of dermatologists is not statistically significant Agreement in Nature of Lesion

| | kappa | Labeille | Chloé | Ravni | CANCER AI |
|---|---|---|---|---|---|
| Cohen's kappa | FF vs Visiomed | 0.41 | 0.39 | 0.4 | 0.58 |
| | FF vs HorusX30 | 0.39 | 0.43 | 0.33 | 0.54 |
| | FF vs HorusX20 | 0.47 | 0.42 | 0.3 | 0.56 |
| | Visiomed vs HorusX30 | 0.39 | 0.48 | 0.39 | 0.45 |
| | Visiomed vs HorusX20 | 0.46 | 0.52 | 0.36 | 0.47 |
| | HorusX30 vs HorusX20 | 0.48 | 0.44 | 0.42 | 0.53 |
| Fleiss' kappa | Global | 0.43 | 0.44 | 0.36 | 0.52 |

| | kappa 95% CI | Labeille | Chloé | Ravni | Cancer AI |
|---|---|---|---|---|---|
| Cohen's kappa | FF vs Visiomed | 0.320-0.504 | 0.300-0.480 | 0.293-0.511 | 0.480-0.660 |
| | FF vs HorusX30 | 0.282-0.490 | 0.339-0.513 | 0.232-0.433 | 0.445-0.631 |
| | FF vs HorusX20 | 0.368-0.567 | 0.333-0.509 | 0.190-0.394 | 0.462-0.647 |
| | Visiomed vs HorusX30 | 0.277-0.495 | 0.378-0.578 | 0.287-0.501 | 0.350-0.545 |
| | Visiomed vs HorusX20 | 0.351-0.568 | 0.430-0.597 | 0.239-0.476 | 0.374-0.559 |
| | HorusX30 vs HorusX20 | 0.372-0.574 | 0.345-0.528 | 0.298-0.533 | 0.441-0.621 |
| Fleiss' kappa | Global | 0.357-0.493 | 0.378-0.501 | 0.291-0.435 | 0.458-0.583 |

Remarks:
  CANCER AI, Labeille, Chlod has moderate agreement while Ravni has fair agreement
  CI of CANCER AI is separated from CI of Ravni=>difference in kappa of AI & Ravni is statistically significant.
  huge overlap between CI of Labeille & Chlod=>difference in kappa of Labeille & Chlod is not statistically significant Agreement in Treatment modality

| | kappa | Labeille | Chloé | Ravni | CANCER AI |
|---|---|---|---|---|---|
| Cohen's kappa | FF vs Visiomed | 0.49 | 0.42 | 0.33 | 0.52 |
| | FF vs HorusX30 | 0.36 | 0.37 | 0.27 | 0.44 |
| | FF vs HorusX20 | 0.41 | 0.46 | 0.25 | 0.51 |
| | Visiomed vs HorusX30 | 0.35 | 0.4 | 0.27 | 0.4 |
| | Visiomed vs HorusX20 | 0.57 | 0.43 | 0.32 | 0.45 |
| | HorusX30 vs HorusX20 | 0.46 | 0.57 | 0.37 | 0.46 |
| Fleiss' kappa | Global | 0.43 | 0.44 | 0.3 | 0.46 |

| | kappa 95% CI | Labeille | Chloé | Ravni | AI |
|---|---|---|---|---|---|
| Cohen's kappa | FF vs Visiomed | 0.381-0.591 | 0.336-0.500 | 0.241-0.434 | 0.435-0.601 |
| | FF vs HorusX30 | 0.256-0.471 | 0.282-0.451 | 0.174-0.363 | 0.361-0.527 |
| | FF vs HorusX20 | 0.304-0.526 | 0.372-0.533 | 0.165-0.342 | 0.414-0.594 |
| | Visiomed vs HorusX30 | 0.246-0.451 | 0.315-0.490 | 0.176-0.369 | 0.306-0.491 |
| | Visiomed vs HorusX20 | 0.449-0.681 | 0.342-0.513 | 0.208-0.427 | 0.356-0.532 |
| | HorusX30 vs HorusX20 | 0.350-0.559 | 0.485-0.639 | 0.268-0.466 | 0.372-0.549 |
| Fleiss' kappa | Global | 0.343-0.513 | 0.383-0.491 | 0.247-0.355 | 0.405-0.520 |

Accuracy of diagnosis hypothesis for separated and combined use of dermoscope

Accuracy=(#correct dx hypothesis)/(#image)

image=972 when consider all images
image=243 when consider each dermoscope or combined use of dermoscope
image=#image of the disease when consider only one disease
correct dx hypothesis is computed under the assumption that
  a. NV=NV_Atyp=NV_Spitz
  b. MEL=MEL_LM=MEL_Meta
95% CI is computed using bootstrap sampling with 1000 repetitions Accuracy on all Images and for Each Disease

| disease | Labeille | Chloé | Ravni | CANCER AI |
|---|---|---|---|---|
| AK | 0 | 0.56 | 0.25 | 0.75 |
| BCC | 0.62 | 0.5 | 0.41 | 0.94 |
| Cyst | 0 | 0.13 | 0 | 0.75 |
| Lentigo | 0.21 | 0.13 | 0.04 | 0.13 |
| MEL | 0.82 | 0.68 | 0.9 | 0.77 |
| NV | 0.42 | 0.68 | 0.45 | 0.77 |
| PAGET | 0 | 0 | 0.25 | 0 |
| SCC | 0 | 0.43 | 0.4 | 0.4 |
| SK | 0.13 | 0.28 | 0.06 | 0.69 |
| all images | 0.58 | 0.59 | 0.57 | 0.77 |
| all images 95% CI | 0.545-0.607 | 0.557-0.616 | 0.542-0.606 | 0.747-0.800 |

Remarks:
  Ravni has highest accuracy on MEL
  Cancer AI has highest accuracy on AK, BCC, Cyst, NV, SK
  Accuracy on all images of Cancer AI is higher than that of dermatologists and this difference is statistical significant.
  There is a slight difference in accuracy on all images of the dermatologists, but this difference is not stats significant.

Accuracy on separated & combined use of dermoscopes Dx hyp for combined use of dermoscopes is defined as follows:
- if 4 answers are all dunno, the final answer is dunno.
- if 4 answers contain only one disease & the rest is dunno, the final answer is that disease.
- if 4 answers contain more than one diseases and there is only one disease X with highest frequency, the final answer is X.
- if 4 answers contain more than one diseases and there is more than one diseases with highest frequency, the final answer is dunno.

Accuracy of nature for separated and combined use of dermoscope.

Sensitivity=(#correct malignant dx)/(#malignant images) where #malignant images=656

Specificity=(#correct benign dx)/(#benign images) where #benign images=316

Accuracy=(#correct nature dx)/(#images)

images=972 if consider all images
images=243 if consider separated or combined use of dermoscope

|  | accuracy | | | | accuracy 95% CI | | | |
| --- | --- | --- | --- | --- | --- | --- | --- | --- |
|  | Labeille | Chloé | Ravni | CANCER AI | Labeille | Chloé | Ravni | CANCER AI |
| FotoFinder | 0.56 | 0.57 | 0.58 | 0.78 | 0.506-0.626 | 0.514-0.630 | 10.510-0.642 | 0.728-0.831 |
| Visiomed | 0.67 | 0.65 | 0.64 | 0.74 | 0.613-0.733 | 0.593-0.708 | 10.584-0.704 | 0.687-0.794 |
| HorusX30 | 0.49 | 0.5 | 0.5 | 0.73 | 0.428-0.551 | 0.440-0.568 | 0.444-0.564 | 0.675-0.786 |
| HorusX20 | 0.52 | 0.56 | 0.53 | 0.74 | 0.457-0.580 | 0.498-0.626 | 0.465-0.584 | 0.683-0.794 |
| combined dermoscope | 0.67 | 0.58 | 0.56 | 0.73 | 0.613-0.728 | 0.514-0.642 | 0.502-0.621 | 0.671-0.782 |

Remarks:
- Among 4 dermoscopes, dermatologists have higher accuracy on Visiomed while A has the highest accuracy on FotoFinder.
- combined use of dermoscopes does not improve accuracy.
- p value is computed by two-tailed z-test, using statsmodels. stats. proportion. proportions_ztest

| p value | Labeille | Chloé | Ravni | CANCER AI |
| --- | --- | --- | --- | --- |
| FF vs Visiomed | 0.015 | 0.078 | 0.164 | 0.29 |
| FF vs HX30 | 0.123 | 0.122 | 0.084 | 0.207 |
| FF vs HX20 | 0.363 | 0.855 | 0.274 | 0.29 |
| FF vs combined | 0.015 | 0.855 | 0.714 | 0.207 |
| Visiomed vs HX30 | 0.0 | 0.001 | 0.002 | 0.838 |
| Visiomed vs HX20 | 0.001 | 0.052 | 0.013 | 1.0 |
| Visiomed vs combined | 1.0 | 0.114 | 0.079 | 0.838 |
| HX30 vs HX20 | 0.525 | 0.173 | 0.525 | 0.838 |
| HX30 vs combined | 0.0 | 0.084 | 0.173 | 1.0 |
| HX20 vs combined | 0.001 | 0.714 | 0.466 | 0.838 |

95% CI is computed using bootstrap sampling with 1000 repetitions

Sensitivity, Specificity, Accuracy on all images

|  | Labeille | Chloé | Ravni | CANCER AI |
| --- | --- | --- | --- | --- |
| specificity | 0.17 | 0.52 | 0.34 | 0.56 |
| sensitivity | 0.78 | 0.54 | 0.86 | 0.82 |
| accuracy | 0.58 | 0.53 | 0.69 | 0.74 |
| accuracy 95% CI | 0.551-0.612 | 0.502-0.567 | 0.663-0.718 | 0.713-0.766 |

Remarks:
- Ravni has highest sensitivity while AI has highest specificity.
- AI has highest accuracy and this difference is stat significant (CI of AI is separated from that of Labeille & Chlod, value of Ravni≠AI is 0.014).

|  | accuracy | | | | accuracy 95% CI | | | |
| --- | --- | --- | --- | --- | --- | --- | --- | --- |
|  | Labeille | Chloé | Ravni | CANCER AI | Labeille | Chloé | Ravni | CANCER AI |
| FotoFinder | 0.57 | 0.47 | 0.67 | 0.74 | 0.506-0.638 | 0.412-0.531 | 0.617-0.733 | 0.687-0.794 |
| Visiomed | 0.66 | 0.6 | 0.73 | 0.76 | 0.597-0.716 | 0.543-0.663 | 0.675-0.778 | 0.704-0.815 |
| HorusX30 | 0.53 | 0.53 | 0.66 | 0.73 | 0.469-0.597 | 0.465-0.589 | 0.601-0.716 | 10.679-0.786 |

|  | accuracy | | | | accuracy 95% CI | | | |
| --- | --- | --- | --- | --- | --- | --- | --- | --- |
|  | Labeille | Chloé | Ravni | CANCER AI | Labeille | Chloé | Ravni | CANCER AI |
| HorusX20 | 0.56 | 0.54 | 0.7 | 0.73 | 0.498-0.621 | 0.481-0.605 | 0.638-0.757 | 0.671-0.790 |
| combined dermoscope | 0.73 | 0.67 | 0.74 | 0.83 | 0.675-0.782 | 0.621-0.733 | 0.687-0.794 | 10.778-0.872 |

Remarks:
Among 4 dermoscopes, dermatologists & Cancer AI have highest accuracy for Visiomed
combined use of dermoscope improves accuracy
p value is computed by two-tailed z-test, using statsmodels.stats.proportion.proportions_ztest

| p value | Labeille | Chloé | Ravni | CANCER AI |
| --- | --- | --- | --- | --- |
| FF vs Visiomed | 0.040 | 0.005 | 0.139 | 0.602 |
| FF vs HX30 | 0.362 | 0.204 | 0.848 | 0.838 |
| FF vs HX20 | 0.855 | 0.123 | 0.435 | 0.838 |
| FF vs combined | 0.000 | 0.000 | 0.092 | 0.016 |
| Visiomed vs HX30 | 0.003 | 0.12 | 0.094 | 0.468 |
| Visiomed vs HX20 | 0.026 | 0.2 | 0.482 | 0.468 |
| Visiomed vs combined | 0.094 | 0.11 | 0.838 | 0.057 |
| HX30 vs HX20 | 0.466 | 0.785 | 0.331 | 1.0 |
| HX30 vs combined | 0.000 | 0.002 | 0.061 | 0.009 |
| HX20 vs combined | 0.000 | 0.004 | 0.364 | 0.009 |

Accuracy of treatment for separated and combined use of dermoscope

Ground truth:
  MEL, BCC, SCC, Paget: biopsy excision
  others: return M3
  Accuracy=(#correct treatment dx)/(#images)
images=972 if consider all images
images=243 if consider separated or combined use of dermoscope
images=656 if consider biopsy excision
images=316 if consider return M3
95% CI is computed using bootstrap sampling with 1000 repetitions
Accuracy on each category and on all images

|  | Labeille | Chloé | Ravni | CANCER AI |
| --- | --- | --- | --- | --- |
| biopsy excision | 1.00 | 0.80 | 0.91 | 0.95 |
| return M3 | 0.13 | 0.61 | 0.40 | 0.56 |
| all images | 0.72 | 0.74 | 0.74 | 0.83 |
| all images 95% CI | 0.687-0.742 | 0.715-0.770 | 0.711-0.769 | 0.801-0.848 |

Accuracy on separated or combined use of dermoscope
NaN values in the answer of dermatologists are replaced by biopsy excision
Treatment dx for combined use of dermoscopes is defined as follows:
  if 4 answers contain only one category, the final answer is that category
  if 4 answers contain both categories, one of them with higher frequency, the final answer is the category with higher frequency
  if 4 answers contain both categories with the same frequency, the final answer is biopsy excision

|  | accuracy | | | | accuracy 95% CI | | | |
| --- | --- | --- | --- | --- | --- | --- | --- | --- |
|  | Labeille | Chloé | Ravni | AI | Labeille | Chloé | Ravni | AI |
| FotoFinder | 0.75 | 0.72 | 0.74 | 0.82 | 0.700-0.807 | 0.663-0.774 | 0.683-0.790 | 0.778-0.868 |
| Visiomed | 0.71 | 0.77 | 0.75 | 0.83 | 0.650-0.770 | 0.716-0.819 | 0.700-0.807 | 0.786-0.877 |
| HorusX30 | 0.70 | 0.73 | 0.72 | 0.80 | 0.638-0.761 | 0.675-0.790 | 0.667-0.778 | 0.757-0.852 |
| HorusX20 | 0.70 | 0.76 | 0.74 | 0.84 | 0.638-0.753 | 0.700-0.807 | 0.691-0.794 | 0.798-0.889 |
| combined dermoscope | 0.70 | 0.78 | 0.75 | 0.83 | 0.634-0.749 | 0.724-0.831 | 0.695-0.798 | 0.782-0.881 |

| p value | Labeille | Chloé | Ravni | CANCER AI |
| --- | --- | --- | --- | --- |
| FF vs Visiomed | 0.308 | 0.177 | 0.756 | 0.812 |
| FF vs HX30 | 0.223 | 0.761 | 0.611 | 0.564 |
| FF vs HX20 | 0.223 | 0.303 | 1.0 | 0.547 |
| FF vs combined | 0.223 | 0.118 | 0.756 | 0.812 |
| Visiomed vs HX30 | 0.843 | 0.295 | 0.412 | 0.416 |
| Visiomed vs HX20 | 0.843 | 0.749 | 0.756 | 0.715 |
| Visiomed vs combined | 0.843 | 0.828 | 1.0 | 1.0 |
| HX30 vs HX20 | 1.0 | 0.468 | 0.611 | 0.239 |
| HX30 vs combined | 1.0 | 0.207 | 0.412 | 0.416 |
| HX20 vs combined | 1.0 | 0.591 | 0.756 | 0.715 |

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

The word "module" or "model" can be also be used interchangeable depending on the context it is described or used in the written description. The "model" can represent one or more artificial intelligence models, machine learning models, or a combination thereof.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with an acne diagnostic mechanism in an embodiment of the present invention. Embodiments of the compute system 100 provide standardized and objective skin cancer detection across 10 classifications and 122 sub-classes, as described earlier.

The 10 classifications include:

MEL: including all types of malignant melanoma such as melanoma in situ, superficial spreading melanoma, nodular melanoma, etc.

BCC: including all types of basal cell carcinoma such as superficial basal cell carcinoma, nodular basal cell carcinoma, basosquamous carcinoma, ulcerated basal cell carcinoma, etc.

EPI: including all types of epidermal pre-malignant and malignant tumors such as actinic keratosis, Bowen disease, squamous cell carcinoma, etc.

MALO: including malignant lesions that are not in MEL, BCC and EPI. This class contains Merkel cell carcinoma, kaposi sarcoma, dermatofibrosarcoma protuberans, etc.

NV: including all types of melanocytic nevus and melanosis.

DF: including all types of dermatofibroma

BAL: including all types of benign adnexal or appendage lesions, such as cystic lesions, pilomatricoma, adenoma, poroma, etc.

BKL: including all types of benign keratinocytic lesions and lentigines such as solar lentigo, seborrheic keratosis, lichen planus-like keratosis, clear cell acanthoma, etc.

VASC: including all types of benign vascular lesions and haemorrhages.

BENO: including all benign lesions that are not in NV, DF, BAL, BKL and VASC.

In examples of embodiment of classification system, malignant lesions are covered in four classes: MEL, BCC, EPI, MALO, while benign lesions are covered in six classes: NV, DF, BKL, VASC, BAL, BENO. Moreover, special sub-classes are separated from others to facilitate the estimation of cancer risk level. For example, Spitz nevus is separated from other benign nevi in the class NV. Pyogenic granuloma is also separated from other benign vascular lesions in the class VASC.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a vehicle, such as a car, truck, bus, motorcycle, or a drone.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description standardized and objective acne scoring of the embodiments of the compute system 100, as an example, the compute system 100 provide functions to various users 112, including patients and clinicians. The compute system 100 can provide functions to the users 112 in a number of ways.

For example, the compute system 100 can provide the functions for the users 112 with the first device 102, the second device 106, distributed between these two devices, or a combination thereof. Also as examples, the compute system 100 can provide a mobile applications for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, patient images 114 are taken and uploaded by the patient and reviewed by a cancer artificial intelligence (AI) module 118 and the clinician. In this embodiment, a patient launches the image based skin cancer detection mechanism via the mobile application and logs into the patient's account. The patient can be prompted to upload or take images as the patient images 114. The compute system 100 can guide a patient on photo guidelines for the patient images 114 and accepts or rejects the patient images 114 for retake based on a pre-specified criteria, e.g., distance, quality, blur, or a combination thereof. The patient images 114 can be selected and processed based on the images uploaded by the user 112.

Once the patient images 114, as required for analysis, are successfully uploaded, the compute system 100 can send or load the patient images 114 to a skin cancer module 116 for analysis. The skin cancer module 116 can include a segmentation module 117. The segmentation module 117 can be a hardware structure managed by software that can identify the perimeter of a lesion identified in the patient image 114 in order to standardize the images being processed. A cancer AI module 118 can be a machine learning or artificial intelligence structure configured to analyze the images provided by the segmentation module 117 and to generate a classification model 119 to identify a skin cancer classification 120 and a risk level assessment 122. For brevity and clarity and as an example, the cancer AI module 118 is shown in FIG. 1 as being executed in the second device 106 although it is understood that portions can operate on the first device 102, such as the mobile app or the web-browser based application, can operate completely on the first device 102, or a combination thereof. As a further example, the cancer AI module 118 can be implemented in software running on specialized hardware, full hardware, or a combination thereof.

The risk level assessment 122 can include a risk level of zero indicating no cancer risk was detected. The risk level assessment 122 of risk level one indicating a precautionary warning, but not active cancer was detected. The risk level 122 can include a risk level two indicating a minor detection of cancer or pre-cancer was detected. The risk level 122 can include a risk level three indicating the detection of a significant risk of cancer has been detected. The risk level 122 can include a risk level four can indicate a risk of melanoma in situ and or non-melanoma skin cancer. The risk level 122 can also include a risk level five indicating a high risk of invasive melanoma or other high grade skin cancers.

Based on analysis results, the compute system 100 can display information to the patient including a recommendation based on the patient images 114, uploaded, for the patient to schedule a visit with your primary care physician or with a specialist based on the skin cancer classification 120, which may or may not be visible or displayed to the user 112.

If the cancer AI module 118 provides the skin cancer module 116 with an indication below a pre-specified level of the risk level assessment 122, the compute system 100 can display a message that based on the patient images 114, uploaded, the user 112 may not need a visit with their primary care physician or with other specialists. The compute system 100 can provide a function allowing the user 112 to schedule a visit with the clinician. The classification model 119 can be a machine learning structure configured to define the criteria for detecting the skin cancer classification 120.

Continuing the example, the compute system 100 can provide a function that allows the clinician to access the patient images 114 uploaded by the user 112 and the skin cancer classification 120, such as the MEL, BCC, EPI, or MALO, through the web-based dashboard from the image based skin cancer detection mechanism. The compute system 100 allows the clinician to make edits to annotations determined by the cancer AI module 118 and the risk level assessment 122 and saves the results. The clinician can utilize the skin cancer classification 120 to make the diagnostic decision and takes necessary treatment steps (if applicable).

In a further embodiment as an example, the compute system 100 can allow a patient to schedule a visit with a primary care physician or with a specialist. A clinician can launch the image based skin cancer detection mechanism, such as a mobile application and logs in. The compute system 100 can be prompted to upload or take the patient images 114 of the patient's body or body parts to be analyzed by the cancer AI module 118.

The compute system 100 can provide guidance to the clinician on the photo guidelines. The compute system 100 can accept or reject images for retake based on a pre-specified criteria, such as distance, quality, blur, or a combination thereof. Once the patient images 114 are successfully uploaded, the compute system 100 and send or load the patient images 114 to the cancer AI module 118 for analysis.

Continuing the example, the compute system 100 can similarly provide a function that allow the clinician to access the patient images 114, uploaded by the user 112, and the skin cancer classification 120, such as with the web-based dashboard from the image based skin cancer detection mechanism. The compute system 100 allows the clinician to make edits to annotations determined by the cancer AI module 118 and the risk level assessment 122 (if necessary) and saves the results. The clinician can utilize the skin cancer classification 120 to make the diagnostic decision and takes necessary treatment steps (if applicable).

Figure 2:
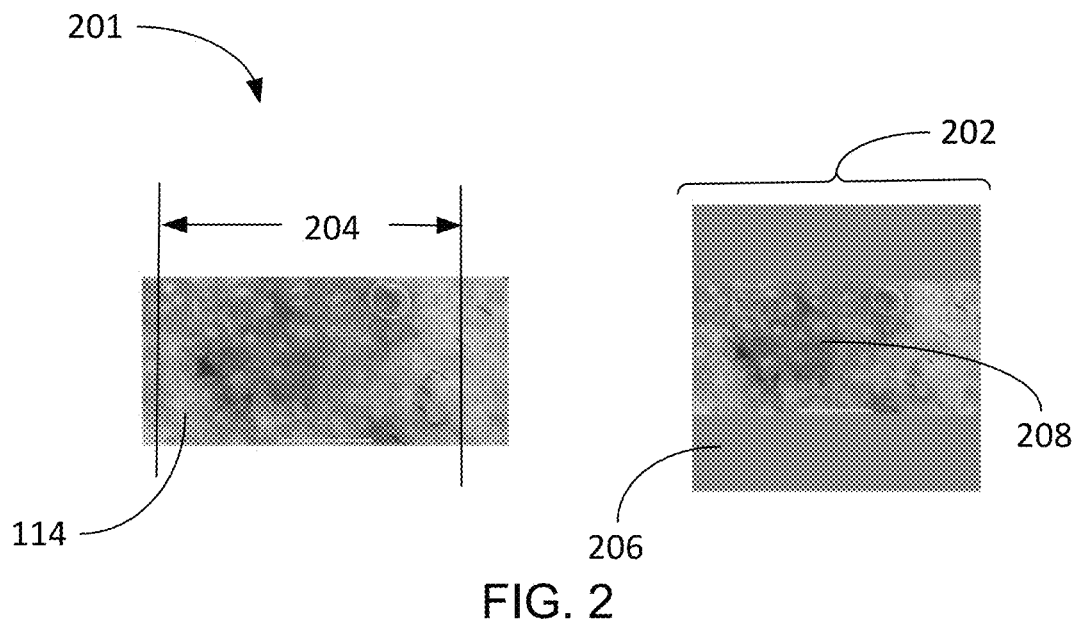
FIG. 2 is an example of center cropping and padding for skin cancer classification in an embodiment.

Referring now to FIG. 2, therein is shown an example of center cropping and padding 201 for the skin cancer classification 120 of FIG. 1 in an embodiment. The compute system 100 of FIG. 1, the cancer AI module 118 of FIG. 1, or a combination thereof can process the patient images 114, such as the leftmost image depicted in FIG. 2. The rightmost image depicted in FIG. 2 is an example of a normalized image 202 that has been center-cropped 204 and padding 206 for analysis.

The segmentation module 117 of FIG. 1 is a hardware structure managed by software and trained on the patient images 114 to automatically detect and segment a skin lesion 208. The segmentation module 117 identifies the perimeter of the skin lesion 208. Then the patient images 114 are center-cropped 204 around the segmented skin lesion 208 with a certain margin, so that the skin lesion 208 lies at the center (see FIG. 1). Average color of the padding 206 might be performed afterward to obtain square images. The combination of the segmentation, center-cropped 204 and the padding 206 is identified as the normalized image 202. The EfficientNetB4 can be utilized with the center-cropped 204 size of 384 pixels by 384 pixels and pretrained weight on ImageNet. The segmentation module 117 of FIG. 1 was trained using NVDIA Titan RTX with starting learning rate 0.0003, learning rate scheduler is the multiplication of starting learning rate and the rate decay (which is 0.985) powers epoch. The segmentation module 117 was trained using ISIC dataset. We use the trained segmentation module 117 to predict on all dataset to obtain a normalized dataset for the classification model 119.

Figure 3:
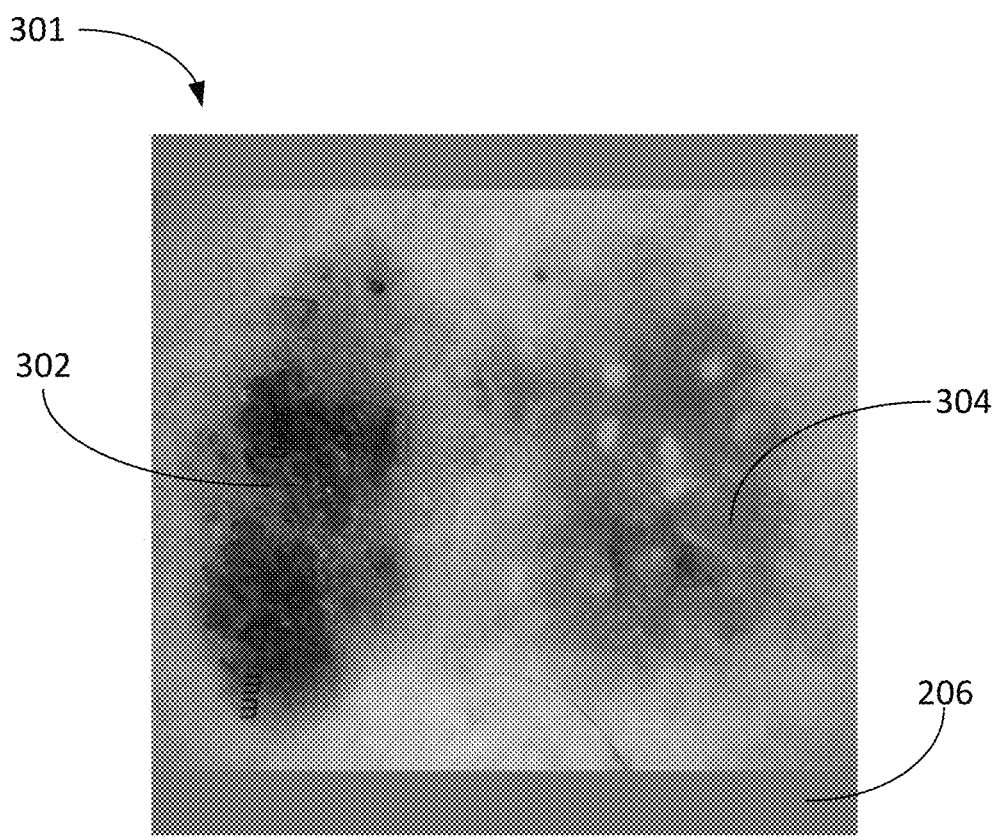
FIG. 3 is an example of a normalized image with a collision of dermoscopic images between two classifications of skin cancer BCC and BKL.

Referring now to FIG. 3, therein is shown an example of a normalized image 301 with a collision of dermoscopic images between two classifications of skin cancer BCC and BKL. An example of the display shown on the display in an embodiment can be on the first device 102, the second device 106, or a combination thereof. The normalized image 301 can include the padding 206 in order to establish the standard size of 384 pixels by 384 pixels.

In this example, the normalized image 301 of the collision of dermoscopic images is shown with the benign lesions of the keratosis type, solar lentigines, seborrheic keratoses, and lichen-planus like keratosis (bkl) 302 adjacent to a basil cell carcinoma 304. In this example, the input is the normalized image 301 including the collision of dermoscopic images as the patient image 114 to the compute system 100, the cancer AI module 118, or a combination thereof.

The configuration of classification model 119 of FIG. 1 is trained to classify a given one of the skin lesion 208 of FIG. 2 into 10 different classes as MEL, BCC, EPI, MALO, NV, DF, BAL, BKL, VASC, or BENO. The classification model 119 can handle multi-label problem that is one image that can belong to two or more classes (collision), type of images that is dermoscopic, macro, or irrelevant. The classification model 119 was trained on normalized images using class and sub-class label. The classification model 119 has a multiplication step (between outputs of class and subclass prediction) to obtain the final subclass prediction. The multiplication step is a specific design in order to obtain a more consistent result, in particular, the subclass prediction output could not exceed the output of class prediction. An improved class prediction can be achieved because the model is forced to learn important features of the sub-class. Sigmoid activation function can be used before output layers are identified because the model can classify one image into more than one class (in collision cases). Since the number of collision images is very low (about 0.38% in our dataset), we create synthetic collision images by putting two images next together in order to verify the identification ability of the classification model 119.

Figure 4:
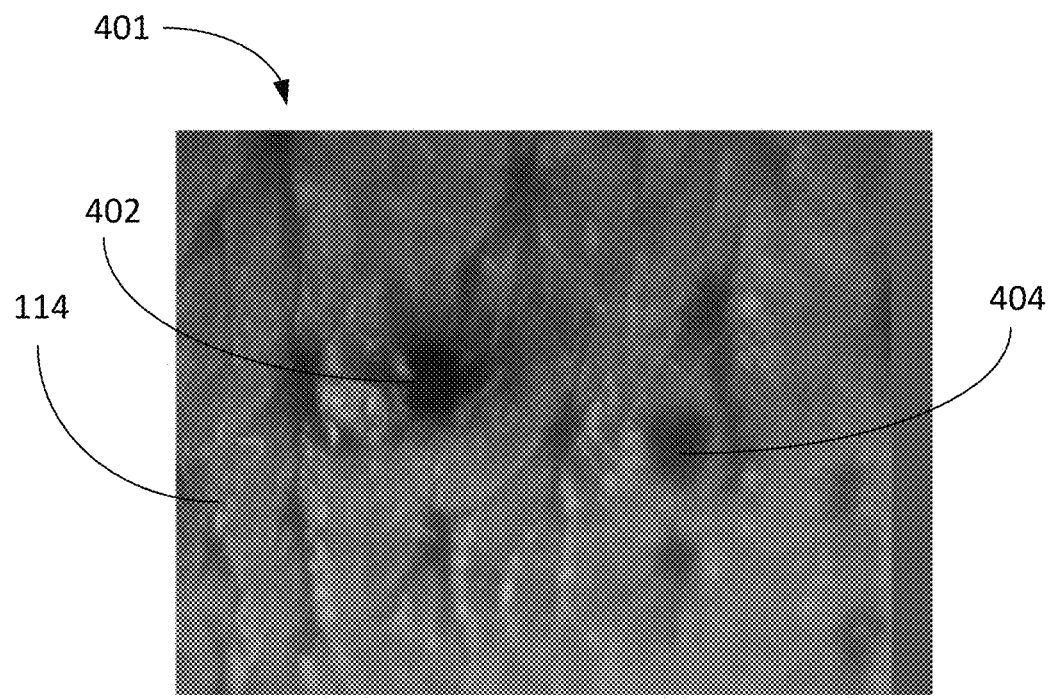
FIG. 4 is an example of the patient image with the collision of dermoscopic images between two classifications of skin cancer identified as BCC and VASC.

Referring now to FIG. 4, therein is shown an example of the patient image 114 with the collision of dermoscopic images 401 between two classifications of skin cancer identified as BCC and VASC. In this example, the patient image 114 can be depicted with the skin cancer classification 120 of FIG. 1 and can be identified by the compute system 100 of FIG. 1, the cancer AI module 118 of FIG. 1, or a combination thereof.

Vascular tumors 402 can be a type of tumor that forms from cells that make blood vessels or lymph vessels. The vascular tumors (VASC) 402 may be benign (not cancer) or malignant (cancer) and can occur anywhere in the body. The vascular tumors 402 may form on the skin, in the tissues below the skin, and/or in an organ. A basil cell carcinoma (BCC) 404 can also be present, which can indicate cancer or pre-cancer.

The compute system 100, the cancer AI module 118, or a combination thereof can be trained to identify each sub-class individually. Once the classification model 119 of FIG. 1 can identify metrics that are greater or higher than a pre-defined threshold for each sub-class, the classification model is considered to be trained. For example, having a Jaccard score higher than 0.8, the compute system 100, the cancer AI module 118, or a combination thereof can be considered to be trained, tested, or a combination thereof as the whole system together. In this training process, a test set is not part of the training set. The test set can include a variety of data for example different skin tone, different cancer types, different resolution, etc. Every time, if any portion of the compute system 100, the cancer AI module 118, or a combination thereof can provide an update, which can be from one model, from one algorithm, the compute system 100, the cancer AI module 118, or a combination thereof can predict the skin cancer classification 120 on those images by running through the image based skin cancer detection mechanism. After the raw results, the compute system 100, the cancer AI module 118, or a combination thereof can run statistical tests and compare the analysis result with the one of the previous version. If the result is better, the compute system 100, the cancer AI module 118, or a combination thereof can keep the update. Otherwise, we will not use it.

Regarding Jaccard score, the Jaccard index, also known as the Jaccard similarity coefficient, is a statistic used for gauging the similarity and diversity of sample sets. It measures the similarity between finite sample sets, it is defined as the ratio of the intersection over the union of the two sets.

$$J(A, B) = \frac{|A \cap B|}{|A \cup B|} \quad (2.4)$$

Figure 5:
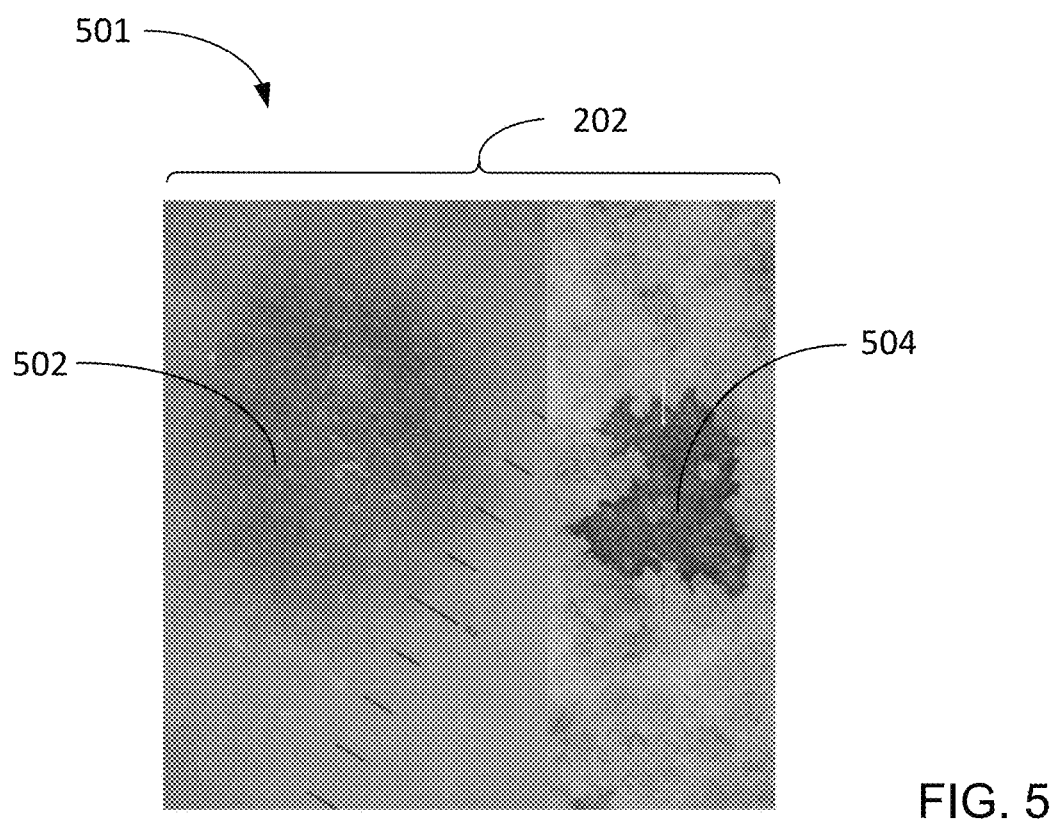
FIG. 5 is an example of the normalized image with a collision of dermoscopic images between two classifications of skin cancer identified as DF and BKL.

Referring now to FIG. 5, therein is shown an example of the normalized image 202 with a collision of dermoscopic images 501 between two classifications of skin cancer identified as DF and BKL. The collision of dermoscopic images 501 depicts the dermatofibroma (DF) 502 and benign keratinocytic lesions (BLK) 504 and can be classified by the compute system 100 of FIG. 1, the cancer AI module 118 of FIG. 1, or a combination thereof.

Figure 6:
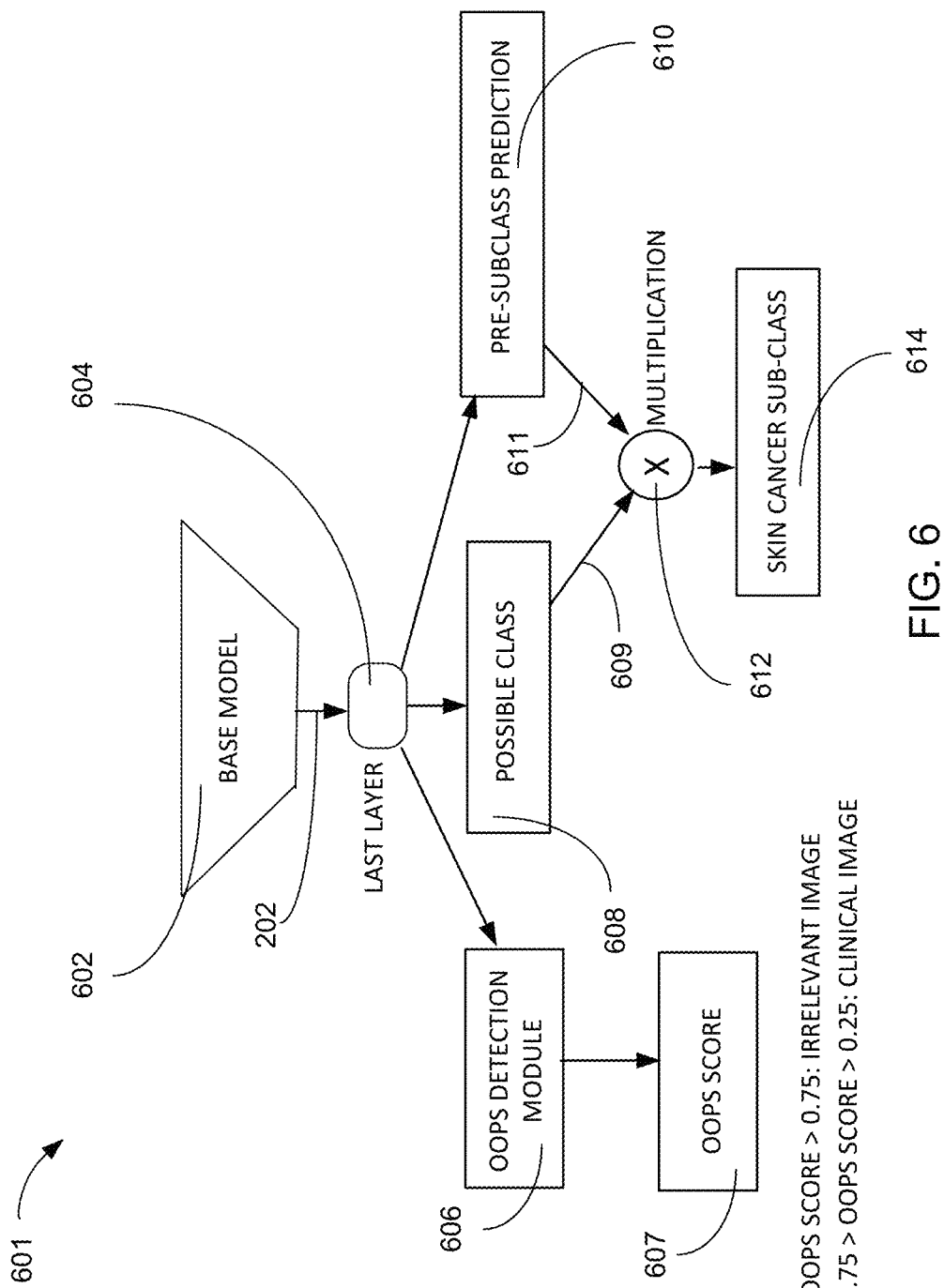
FIG. 6 is a functional block diagram of the classification model in subclass-based approach in an embodiment.

Referring now to FIG. 6, therein is shown a functional block diagram 601 of the classification model 119 in sub-class-based approach in an embodiment. The functional block diagram 601 depicts a base model 602 producing a last layer 604. The training pipeline contains two major steps: segmentation and classification. The classification model 119 is not directly trained on the patient images 114 of FIG. 1 because: the skin lesion 208 of FIG. 2 might be too small compared with the rest part of the patient image 114, the skin lesion 208 might be displaced off-center, and other details than the skin lesion 208 might confuse the classification model 119. Therefore, the base model 602 first runs the segmentation module 117 of FIG. 1 then center-crop the detected skin lesion 208 in order to generate the normalized image 202. The classification model 119 can operate on the normalized image 202 to produce the last layer 604.

In this example, the flow can progress from an oops detection module 606 to produce an oops score 607. Continuing the example, the oops detection module 606 can perform an image quality check and can function as a filter for preventing bad quality images to be used as input for the classification model 119. The oops score 607 can indicate the quality of images that are too blurry or images that are of poor luminosity (either too bright, too dark or too noisy). The oops score 607 greater that 0.75 indicates the normalized image 202 is irrelevant and should not be used for analysis. The oops score 607 that is less than or equal to 0.75 an greater than 0.25 indicates a clinical image that is acceptable for analysis by the classification model 119. It is also determined that the oops score 607 less than or equal to 0.25 indicated the normalized image 202 is acceptable for training the classification model 119.

For example, the oops detection module 606 can check the patient images 114 of FIG. 1 that are input for certain quality criteria and meeting or exceeding a quality threshold. As a specific example, if an instance of the patient images 114 is relevant or usable to compute the skin cancer module 116, then the oops detection module 606 determined that instance of the normalized images 202 continues processing.

The classification model 119 was trained using ISIC dataset. For the ISIC dataset, with the help from doctors, about 30% have sub-class labels. Moreover, there are several duplicate images in ISIC dataset, which can be identified by the classification model 119 to find all possible duplicates of the normalized images 202.

The last layer 604 can be coupled to a class estimation module 608 and a pre-subclass prediction module 610. The class estimation module 608 can be a hardware structure configured to estimate the class of the skin lesion 208 in the normalized images 202. The class estimation module 608 can calculate a class prediction 609, for indicating the class of the skin lesion 208 identified in the normalized image 202. The pre-subclass estimation module 610 can be a hardware structure configured to match the normalized image 202 with a sub-class prediction 611. The output of the class estimation module 608 and the pre-subclass prediction module 610 can be inputs to a multiplier 612 that can produce a skin cancer sub-class 614 that corresponds to each of the class prediction 609.

The multiplier 612 can be a hardware structure configured to multiply the class prediction 609 with the subclass prediction 611 in order to obtain a more consistent result. The classification model 119 is taught to identify important features in the normalized images 202 to correctly identify the class prediction 609 and the subclass prediction 611. The classification model can also identify any duplicates of the normalized images 202 in the training dataset and the validation dataset.

It has been discovered that the use of the multiplier 612 can improve the reliability of the class prediction 609 and the subclass prediction 611 across the normalized images 202. The improved reliability of the classification model 119 can be demonstrated by a comparison of the detection capabilities of the compute system 100 of FIG. 1, the cancer AI module 118 of FIG. 1, or a combination thereof.

Figure 7:
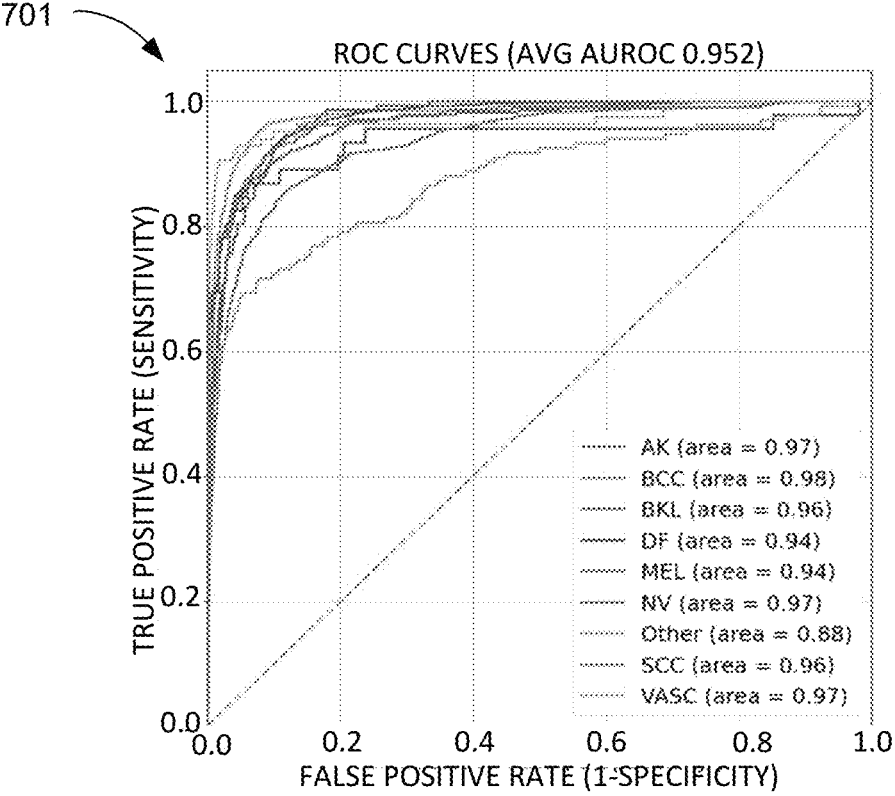
FIG. 7 is an example of a receiver operating characteristic (ROC) validation curve for each skin cancer classification.

Referring now to FIG. 7, therein is shown an example of a receiver operating characteristic (ROC) validation curve 701 for each of the skin cancer classification 120. The compute system 100, the cancer AI module 118, or a combination thereof can implemented in an number of ways. For example, the oops module 606 of FIG. 6 can be implemented with an Inception-ResNet-v2 convolutional neural network, which was pre-trained with the ImageNet data set, for the encoding part.

A blind test of the Cancer AI 118 has been applied to 4926 dermatoscopic skin images collected by the Trieste team during their practice. The Trieste test set was classified into nine classes: MEL, BCC, SCC, AK, NV, BKL, DF, VASC, and Other. The test results are summarized in Table 1. A sensitivity of 93% (resp. 80%) and a specificity of 70% (resp. 92%) for MEL when using the cutoff threshold of 0.18 (resp. 0.50).

A threshold of 0.18 for MEL means that any image with MEL score above 0.18 is considered to have significant melanoma risk. Test results compare favorably to the performance of dermatologists. The sensitivity—specificity of dermatologists for dermatoscopic image-based melanoma detection is only sensitivity of 67% —specificity of 62% versus Cancer AI 118 sensitivity of 93% —specificity of 70%.

TABLE 1

| Summary of validation result on the ItoBos test set | | | | | | | | | | |
|---|---|---|---|---|---|---|---|---|---|---|
| Class | MEL | MEL | BCC | SCC | AK | NV | BKL | DF | VASC | Other |
| # Images | 868 | 868 | 697 | 211 | 148 | 2422 | 283 | 46 | 85 | 134 |
| AUROC | 0.94 | 0.94 | 0.98 | 0.96 | 0.97 | 0.97 | 0.96 | 0.94 | 0.97 | 0.88 |
| Sens (%) | 93 | 80 | 95 | 88 | 84 | 75 | 80 | 70 | 89 | 86 |
| SPEC (%) | 70 | 92 | 92 | 93 | 93 | 97 | 97 | 99 | 98 | 67 |
| THRESHOLD | 0.18 | 0.5 | 0.18 | 0.18 | 0.18 | 0.82 | 0.49 | 0.18 | 0.18 | 0.06 |

The results shown in Table 1 indicate a high reliability of the performance of the D cancer AI 118 in processing a validation data set. The performance of the cancer AI 118 can out perform a clinician in most cases.

Figure 8:
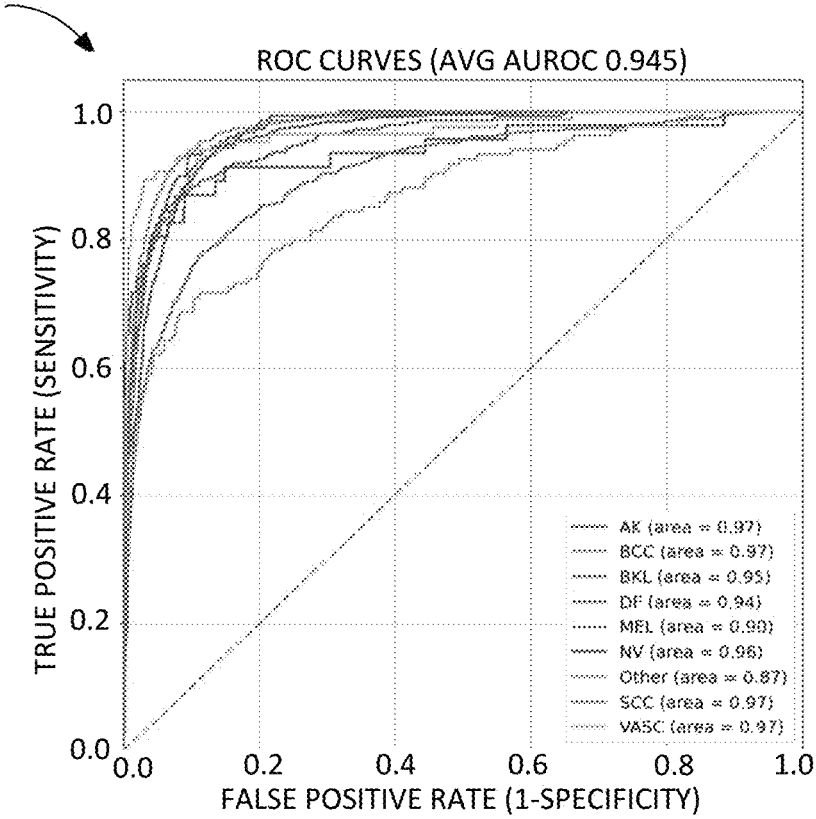
FIG. 8 is an example of a receiver operating characteristic (ROC) validation curve for each of the skin cancer classification with sub-class label training.

Referring now to FIG. 8, therein is shown an example of a receiver operating characteristic (ROC) validation curve 801 for each of the skin cancer classification 120 with subclass label training. The ROC curves 801 and AUROC for each class model trained with sub-class label. It has been discovered that the model trained with subclass label has higher average AUROC and better performance.

The training data set includes approximately 30% of the normalized images 202 of FIG. 2 include sub-class labels. By training the cancer AI 118 of FIG. 1 with the sub-class labels can provide increased reliability of the detection of the skin cancer classification 120 of FIG. 1.

Figure 9:
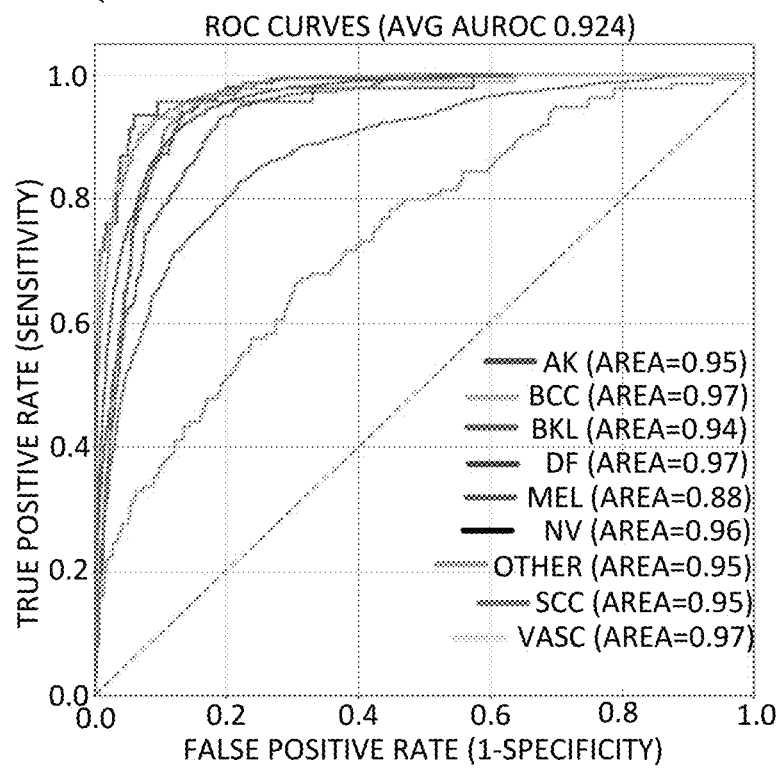
FIG. 9 is an example of a receiver operating characteristic (ROC) validation curve for each of the skin cancer classification without sub-class label training.

Referring now to FIG. 9, therein is shown is an example of a receiver operating characteristic (ROC) validation curve 901 for each of the skin cancer classification without sub-class label training.

The compute system 100 of FIG. 1 with the image based skin cancer detection mechanism, has the following three distinctive features: a large, diversified learning dataset of about 100 thousand images, a granular hierarchical class/sub-class classification, and innovative loss functions. The hierarchical classification system helps the cancer AI 118 of FIG. 1 learn better and become more robust. The Cancer AI 118 that can detect not only 10 different classes included MEL, BCC, EPI, MALO, NV, DF, BAL, BKL, VASC and BENO but also 122 sub-class for example Melanoma in situ, Melanoma nodular, etc. We use hierarchical learning (class and sub-class) which gives more accurate result then training with class information only. The system includes two steps: segmentation of the skin lesion 208 of FIG. 2 and classification of the skin lesion 208. With this type of learning, each of the skin lesion 208 has two labels, one for class and the other for sub-class (or sub-type). If the skin lesion 208 does not have sub-class information, we will set the gradient be zero so that it will not affect the back-propagation process. A blind test using a test set of 4926 images provided an average of 0.95 of AUC (area under the curve) and 0.94 for MEL, 0.97 for NV, and 0.98 for BCC.

Figure 10:
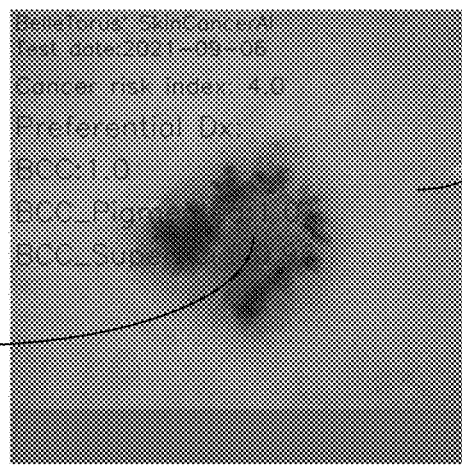
FIG. 10 is an example of a skin cancer display for analysis of Basil Cell Carcinoma as performed by cancer AI in an embodiment.

Referring now to FIG. 10, therein is shown an example of a skin cancer display 1001 for analysis of Basil Cell Carcinoma 1002 as performed by cancer AI module 118 of FIG. 1 in an embodiment. The compute system 100, the cancer AI module 118, or a combination thereof can be trained for 95 epochs with substantially 40000 images in each epoch, about 80% of the data set is reserved for training set and 20% of the data set is for validation.

The analysis of the normalized image 202 of Basil Cell Carcinoma 1002 as performed by cancer AI module 118 depicts the risk level assessment 122, the skin cancer classification 120, and a skin cancer sub-class 1004. The risk level assessment 122 can indicate a level four indication provides a significant risk of pre-cancer or potential early cancer that should be addressed by a clinician.

Figure 11:
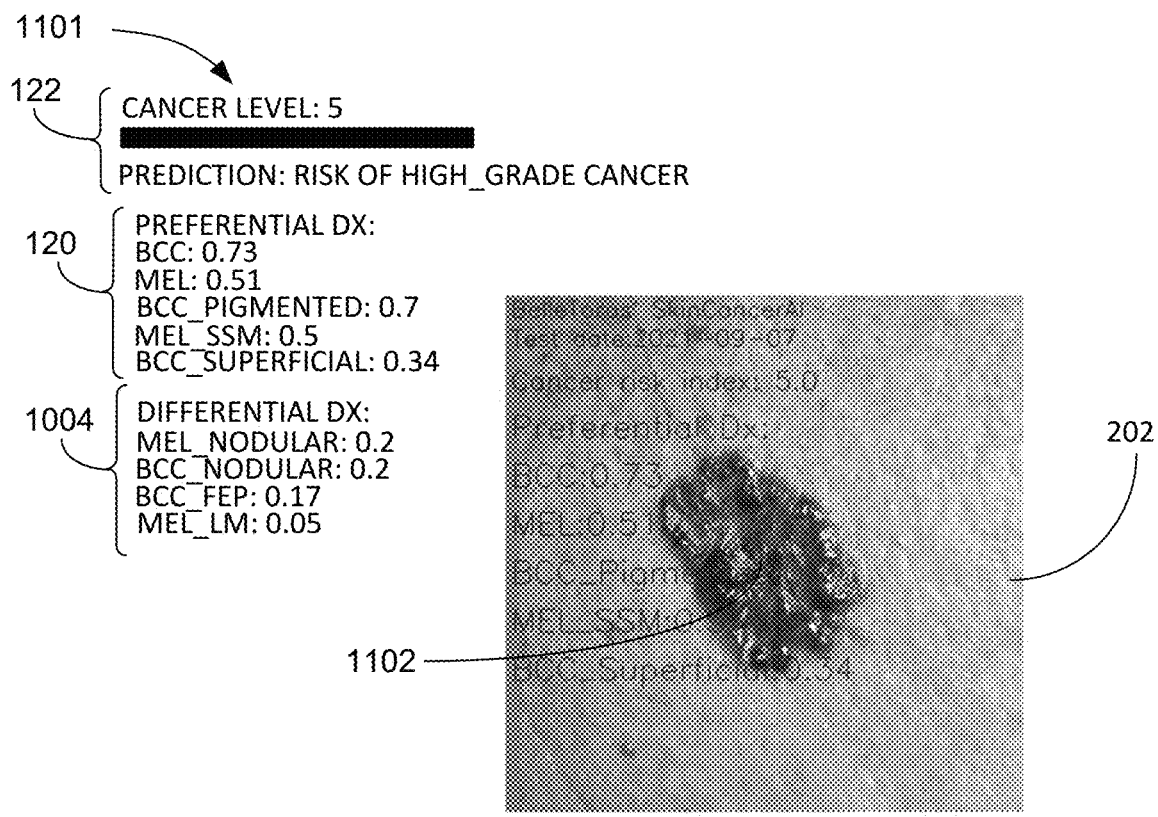
FIG. 11 are examples of a skin cancer display for analysis of an alternate form of Basil Cell Carcinoma as identified by cancer AI in an embodiment.

Referring now to FIG. 11, therein are shown examples of a skin cancer display 1101 for analysis of an alternate form of Basil Cell Carcinoma 1102 as identified by cancer AI 118 of FIG. 1 in an embodiment. The normalized image 202 has a complete analysis of the basil cell carcinoma 1102 as predicted by the cancer AI 118.

The analysis of the normalized image 202 of Basil Cell Carcinoma 1102 as performed by cancer AI 118 depicts the risk level assessment 122, the skin cancer classification 120, and the skin cancer sub-class 1004. The risk level assessment 122 can indicate a level five indication provides a high risk of cancer that should be addressed by a clinician.

Figure 12:
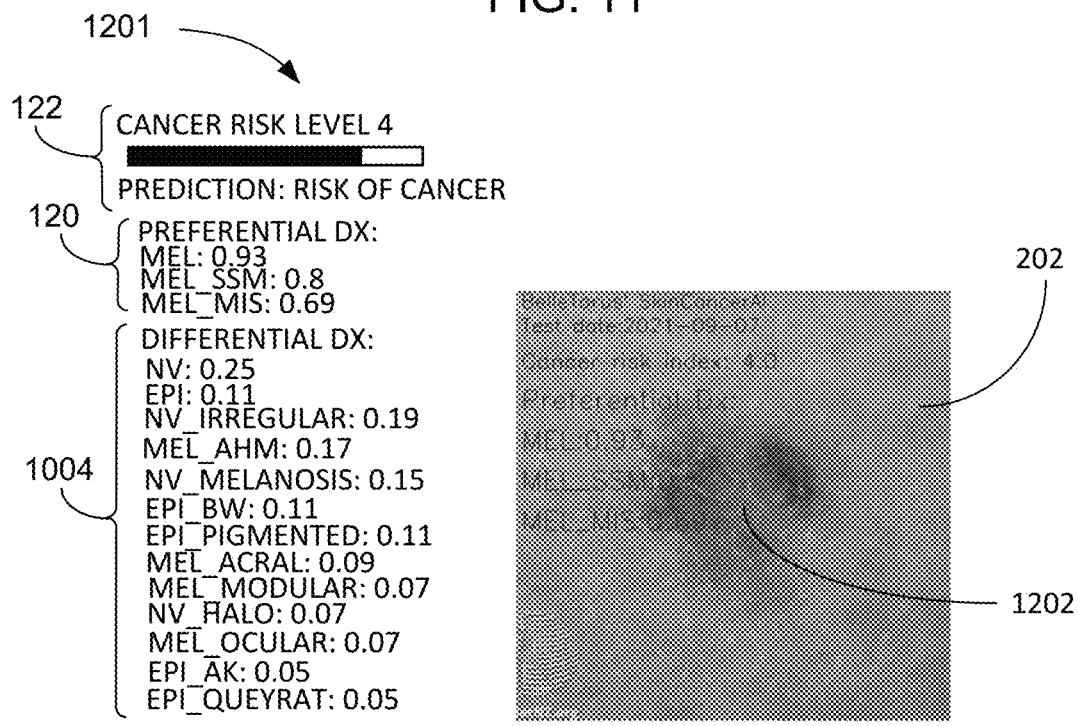
FIG. 12 is an example of a skin cancer display for analysis of a Melanoma cancer as performed by cancer AI in an embodiment.

Referring now to FIG. 12, therein are shown an example of a skin cancer display 1201 for analysis of a Melanoma cancer 1202 as performed by cancer AI 118 of FIG. 1 in an embodiment. The normalized image 202 has a complete analysis of the melanoma cancer 1202 as predicted by the cancer AI 118.

The analysis of the normalized image 202 of the melanoma cancer 1202 as performed by cancer AI 118 depicts the risk level assessment 122, the skin cancer classification 120, and the skin cancer sub-class 1004. The risk level assessment 122 can indicate a level four indication provides a substantial risk of cancer that should be addressed by a clinician.

Figure 13:
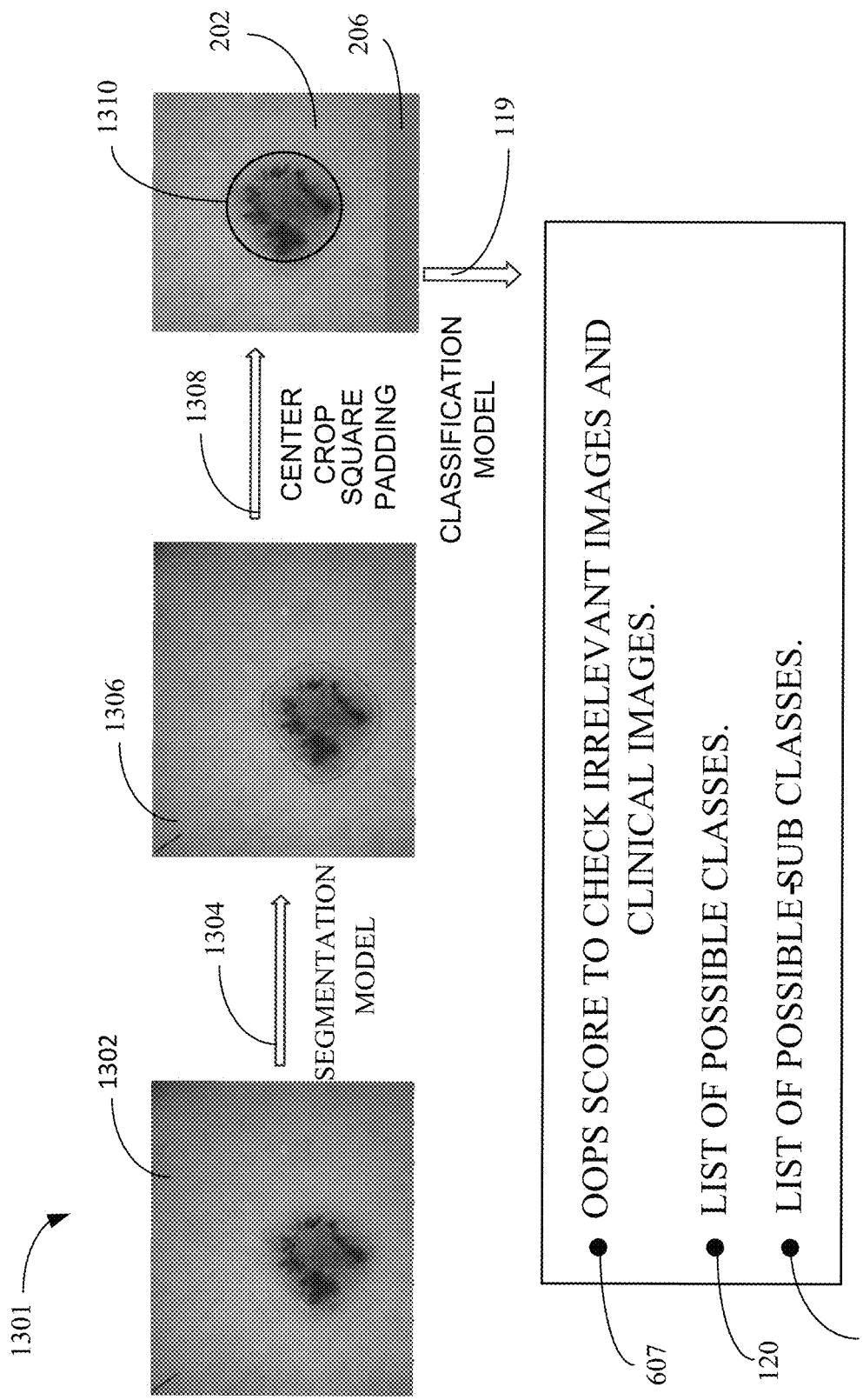
FIG. 13 is an example of a flow diagram of a skin cancer analysis in an embodiment.

Referring now to FIG. 13, therein are shown an example of a flow diagram 1301 of a skin cancer analysis in an embodiment. The flow diagram 1301 depicts generating an oops score in a block 1302, which is processed through a segmentation module 1304 to produce a segmented image 1306. The segmented image 1306 can be processed by a center crop and padding process 1308 to produce the normalized image 202 including the skin lesion 208 at the center 1310 and the padding 206. The normalized image 202 is then submitted to the cancer AI 118 of FIG. 1 for generating skin cancer classification 120 of FIG. 1. The classification model 119 can provide the oops score 607, the list of possible classes 120, and list of possible sub-classes 1004.

Figure 14:
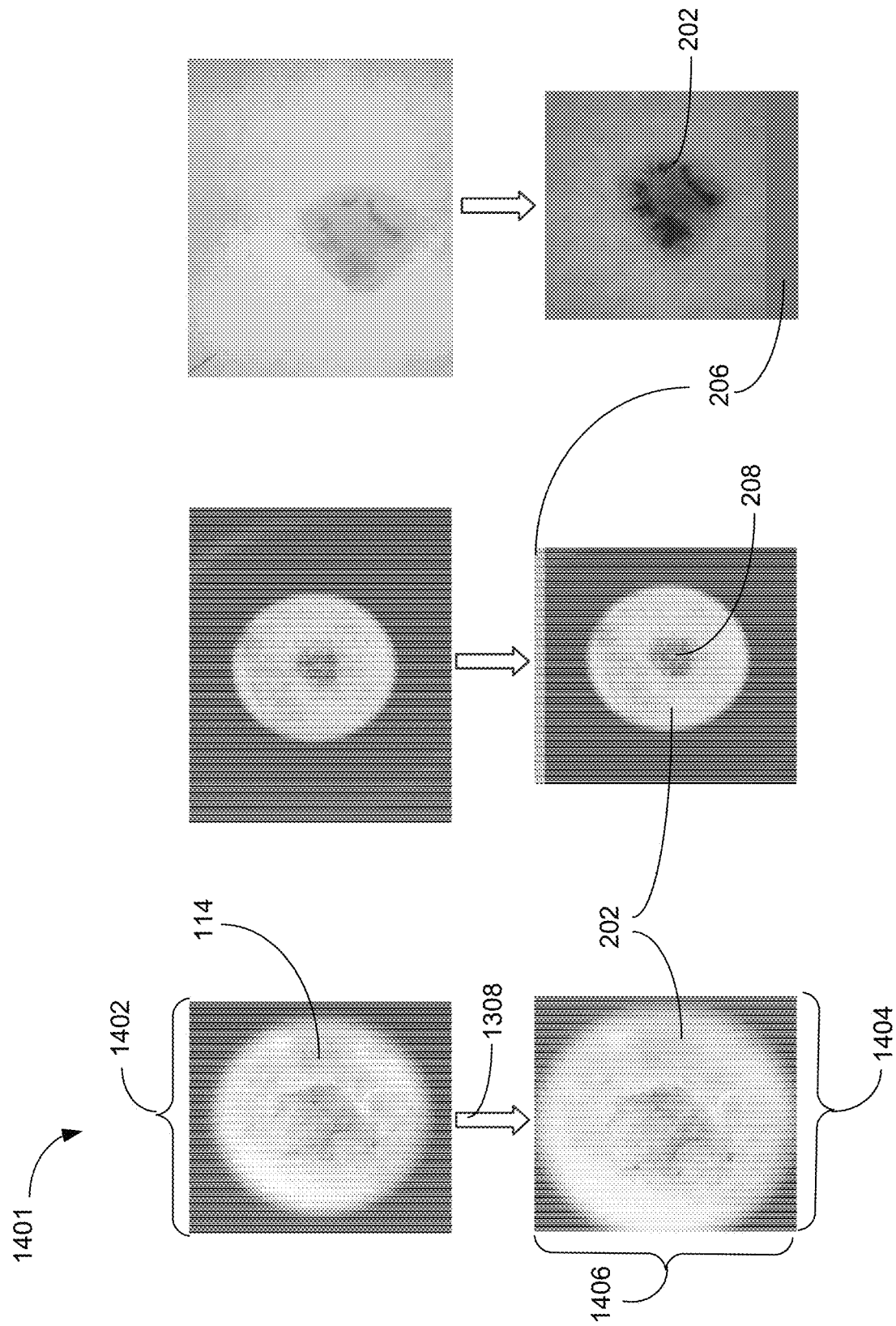
FIG. 14 is an example of an image center crop and padding process in an embodiment.

Referring now to FIG. 14, therein is shown an example of an image center crop and padding process 1401 in an embodiment. The production of the normalized images 202 relies on the center crop and padding process 1308. An input width 1402 can be below the standard size of the normalized images 202. The center crop and padding process 1308 can adjust the input width 1402 to match the normalized width 1404 of 384 pixels. The center crop and padding process 1308 also adjusts the normalized height 1406 to match the normalized width 1404.

In case the patient image 114 is larger than the normalized image 202, the center crop and padding process 1308 can crop the patient image 114 in order to meet the normalized width 1404 and add the padding 206 to establish the normalized height 1406 with the skin lesion 208 at the center 1310 of FIG. 13.

Figure 15:
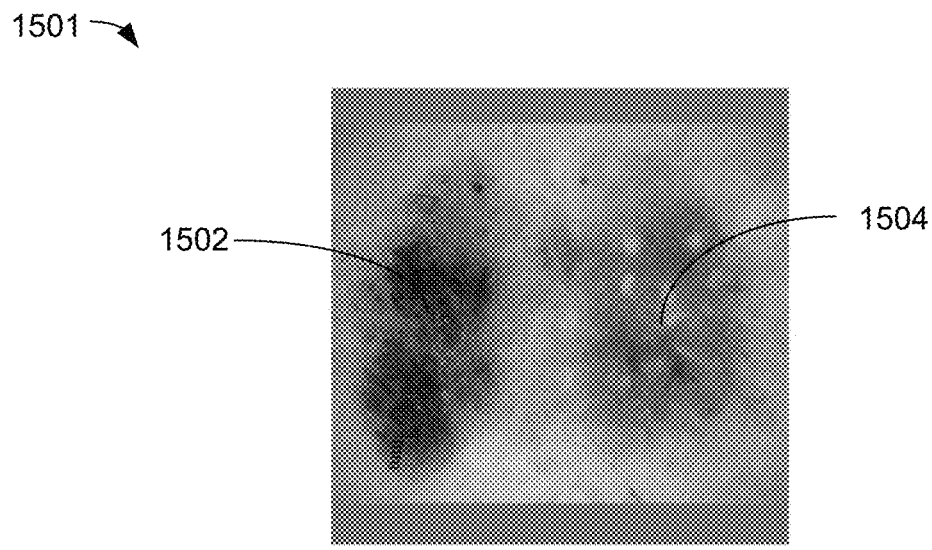
FIG. 15 is an example of skin cancer collision and the classification in an embodiment.

Referring now to FIG. 15, therein is shown an example of skin cancer collision 1501 and the classification in an embodiment. Skin Cancer classification 120 of FIG. 1 is primarily of one class output. Very rarely collision cases can occur (383/100,000 images ~0.38%). The cancer AI 118 of FIG. 1 can be trained to predict at least two classes in this situation. The classification model 119 of FIG. 1 can identify the BCC 1502 and the BKL 1504

Figure 16:
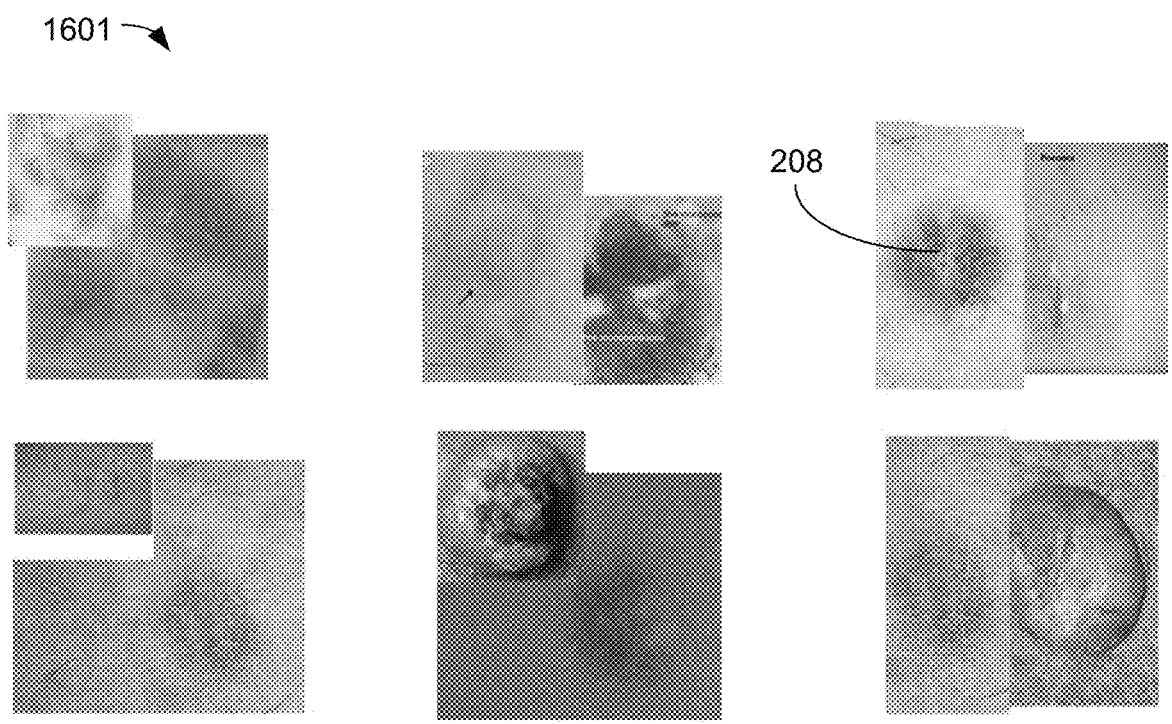
FIG. 16 is an example of a collision images of skin cancer collision for testing the cancer AI in an embodiment.

Referring now to FIG. 16, therein is shown an example of a collision images 1601 of skin cancer collisions for testing the cancer AI 118 of FIG. 1 in an embodiment. These samples of diverse types of skin cancer have been created as a training and test case for the cancer AI 118.

In order to train the cancer AI 118, the manufacture of the collision images 1601 can combine two or more known skin conditions including the skin lesions 208. In processing the collision images 1601, the classification model 119 of FIG. 1 can identify more than one of the skin lesions 208 in each of the collision images 1601.

Figure 17:
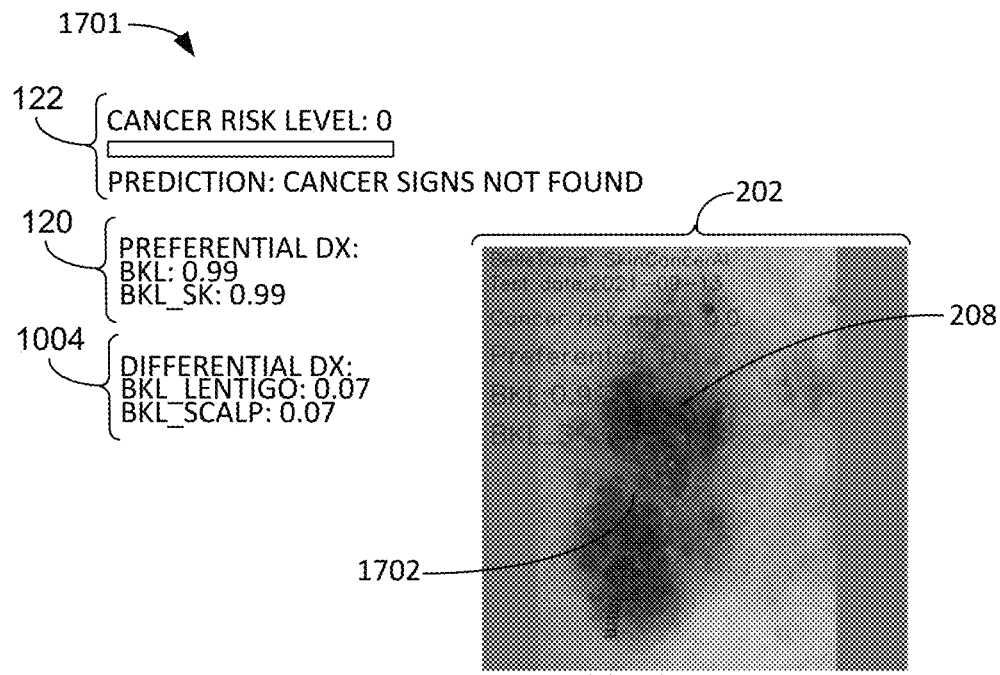
FIG. 17 is an example of a skin cancer display of one half of the skin cancer collision of FIG. 15.

Referring now to FIG. 17 therein is shown an example of a skin cancer display 1701 of one half of the skin cancer collision 1501 of FIG. 15. The cancer AI 118 of FIG. 1 is capable of isolating and analyzing the benign lesions of the keratosis (BKL) 1702 separate from the melanoma (MEL) that is shown in an adjacent location in FIG. 15.

The skin cancer display 1701 depicts the risk level assessment 122 indicating no cancer risk from the BKL 1702. The skin cancer classification 120 identifies the skin lesion 208 in the normalized image 202 as the benign lesions of the keratosis (BKL) 1702. The skin cancer display 1701 also provides the skin cancer sub-class 1004 indicating the possible sub-class of the BKL 1702.

Figure 18:
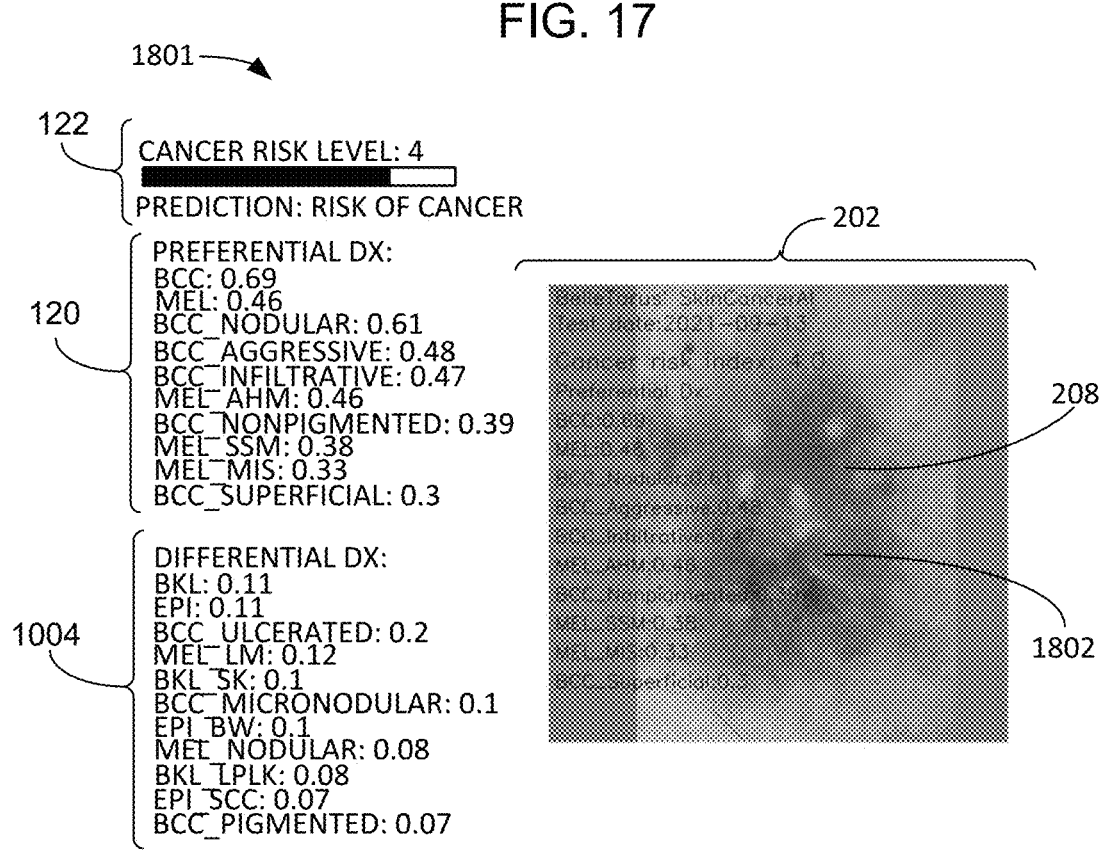
FIG. 18 is an example of an analysis of a second half of the skin cancer collision of FIG. 15.

Referring now to FIG. 18, therein an example of a skin cancer display 1801 of a second half of the skin cancer collision 1501 of FIG. 15. The cancer AI 118 of FIG. 1 is capable of isolating and analyzing the melanoma (MEL) separate from the BKL that is shown in an adjacent location in FIG. 15.

The skin cancer display 1801 depicts the risk level assessment 122 indicating significant cancer risk from the BCC or the MEL 1802. The skin cancer classification 120 identifies the skin lesion 208 in the normalized image 202 as the basil cell carcinoma (BCC) or the melanoma cancer (MEL) 1802. The skin cancer display 1801 also provides the skin cancer sub-class 1004 indicating the possible sub-class of the skin lesion 208.

Figure 19:
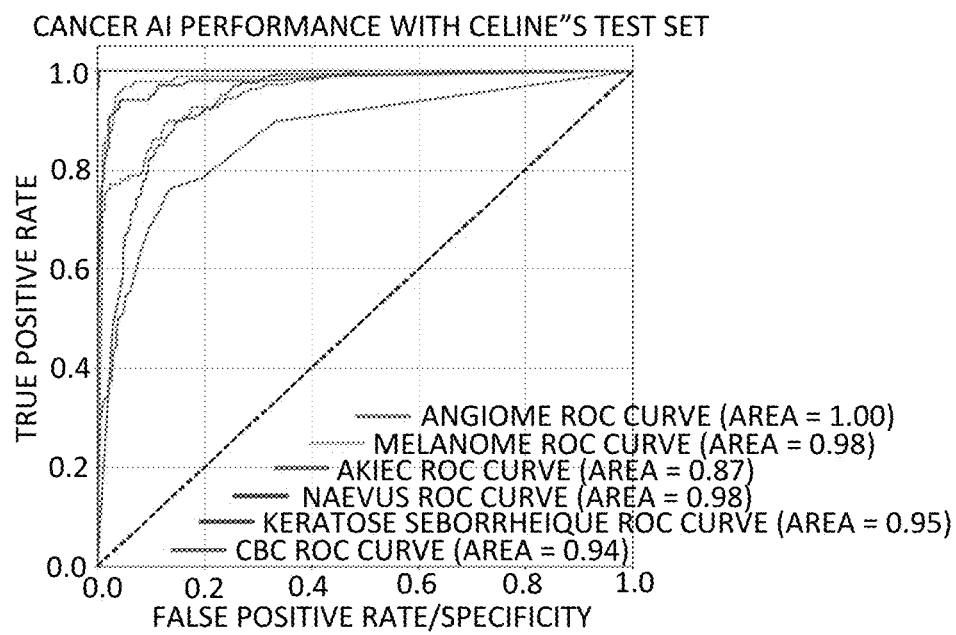
FIG. 19 is an example of a receiver operating characteristic (ROC) validation curve for each class of skin cancer identified in the 653 image test set.

Referring now to FIG. 19, therein is shown an example of a receiver operating characteristic (ROC) validation curve 1901 for each class of skin cancer identified in the 653 images of the Celine's test set. The ROC validation curve 1901 indicates the proficiency of the cancer AI 118 of FIG. 1 in identifying the individual cancers represented in the Celine's test set used as a validation of the capabilities of cancer identification mechanisms.

Figure 20:
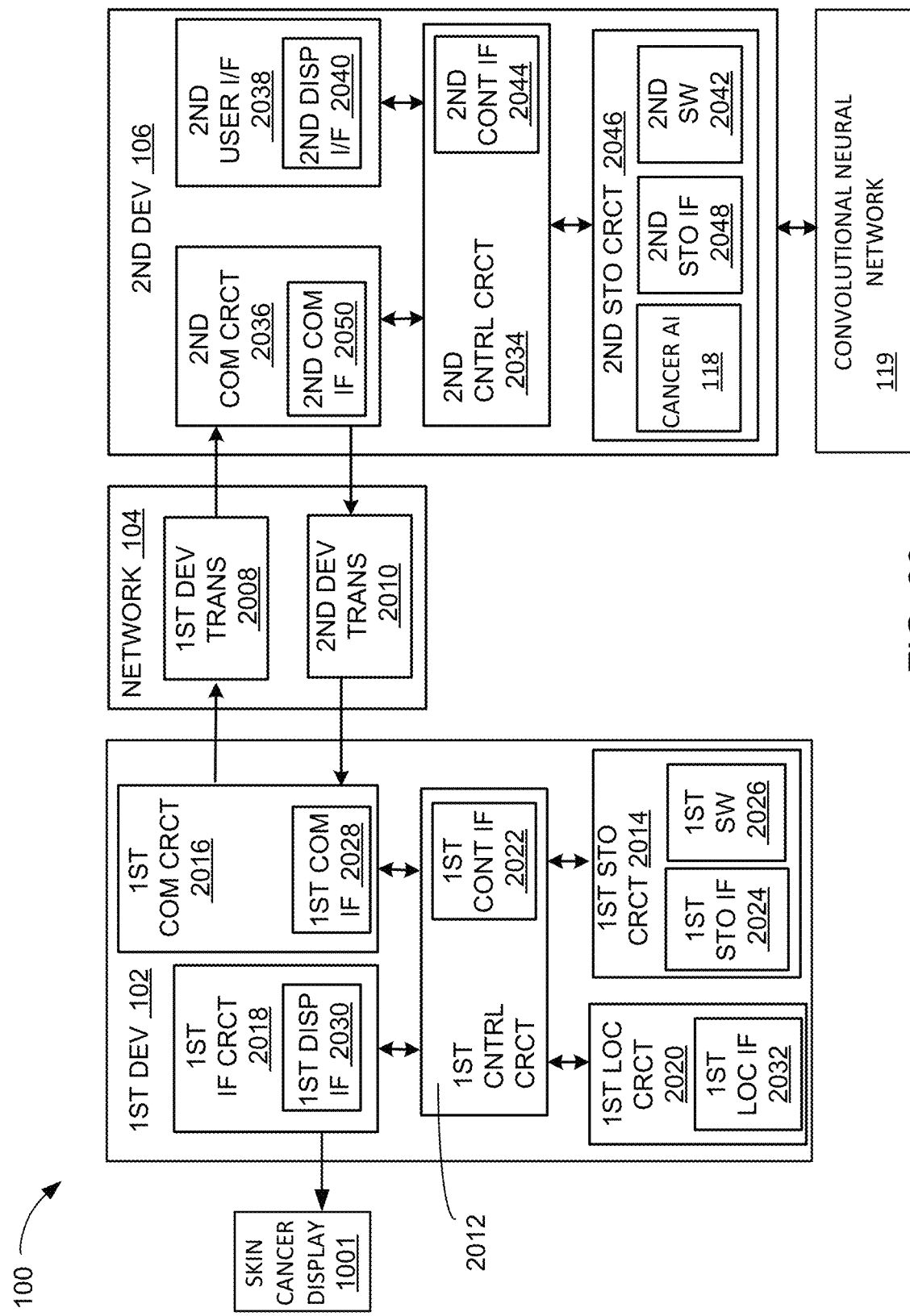
FIG. 20 is an exemplary block diagram of the compute system in an embodiment.

Referring now to FIG. 20, therein is shown an exemplary block diagram of the compute system 100 in an embodiment. The compute system 100 can include the first device 102, the network 104, and the second device 106. The first device 102 can send information in a first device transmission 2008 over the network 104 to the second device 106. The second device 106 can send information in a second device transmission 2010 over the network 104 to the first device 102.

For illustrative purposes, the compute system 100 is shown with the first device 102 as a client device, although it is understood that the compute system 100 can include the first device 102 as a different type of device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102.

Also, for illustrative purposes, the compute system 100 is shown with interaction between the first device 102 and the second device 106. However, it is understood that the first device 102 can be a part of or the entirety of an autonomous vehicle, a smart vehicle, or a combination thereof. Similarly, the second device 106 can similarly interact with the first device 102 representing the autonomous vehicle, the intelligent vehicle, or a combination thereof.

For brevity of description in this embodiment of the present invention, the first device 102 will be described as a client device, the vehicle 201, and the second device 106 will be described as a server device. The embodiment of the present invention is not limited to this selection for the type of devices. The selection is an example of an embodiment of the present invention.

The first device 102 can include a first control circuit 2012, a first storage circuit 2014, a first communication circuit 2016, a first interface circuit 2018, and a first location circuit 2020. The first control circuit 2012 can include a first control interface 2022. The first control circuit 2012 can execute a first software 2026 to provide the intelligence of the compute system 100.

The first control circuit 2012 can be implemented in a number of different manners. For example, the first control circuit 2012 can be a processor, an application specific integrated circuit (ASIC) an embedded processor, a microprocessor, a hardware control logic, a hardware finite state machine (FSM), a digital signal processor (DSP), or a combination thereof. The first control interface 2022 can be used for communication between the first control circuit 2012 and other functional units or circuits in the first device 102. The first control interface 2022 can also be used for communication that is external to the first device 102.

The first control interface 2022 can receive information from the other functional units/circuits or from external sources, or can transmit information to the other functional units/circuits or to external destinations. The external sources and the external destinations refer to sources and destinations external to the first device 102.

The first control interface 2022 can be implemented in different ways and can include different implementations depending on which functional units/circuits or external units/circuits are being interfaced with the first control interface 2022. For example, the first control interface 2022 can be implemented with a pressure sensor, an inertial sensor, a microelectromechanical system (MEMS), optical circuitry, waveguides, wireless circuitry, wireline circuitry, or a combination thereof.

The first storage circuit 2014 can store the first software 2026. The first storage circuit 2014 can also store the relevant information, such as data representing incoming images, data representing previously presented image, sound files, or a combination thereof.

The first storage circuit 2014 can be a volatile memory, a nonvolatile memory, an internal memory, an external memory, or a combination thereof. For example, the first storage circuit 2214 can be a nonvolatile storage such as non-volatile random-access memory (NVRAM), Flash memory, disk storage, or a volatile storage such as static random-access memory (SRAM).

The first storage circuit 2014 can include a first storage interface 2024. The first storage interface 2024 can be used for communication between the first storage circuit 2014 and other functional units or circuits in the first device 102. The first storage interface 2024 can also be used for communication that is external to the first device 102.

The first storage interface 2024 can receive information from the other functional units/circuits or from external sources, or can transmit information to the other functional units/circuits or to external destinations. The external sources and the external destinations refer to sources and destinations external to the first device 102. The first storage interface 2024 can receive input from and source data to the cancer AI module 118.

The first storage interface 2024 can include different implementations depending on which functional units/circuits or external units/circuits are being interfaced with the first storage circuit 2014. The first storage interface 2024 can be implemented with technologies and techniques similar to the implementation of the first control interface 2022.

The first communication circuit 2016 can enable external communication to and from the first device 102. For example, the first communication circuit 2016 can permit the first device 102 to communicate with the second device 106 and the network 104.

The first communication circuit 2016 can also function as a communication hub allowing the first device 102 to function as part of the network 104 and not limited to be an endpoint or terminal circuit to the network 104. The first communication circuit 2016 can include active and passive components, such as microelectronics or an antenna, for interaction with the network 104.

The first communication circuit 2016 can include a first communication interface 2028. The first communication interface 2028 can be used for communication between the first communication circuit 2016 and other functional units or circuits in the first device 102. The first communication interface 2028 can receive information from the second device 106 for distribution to the other functional units/circuits or can transmit information to the other functional units or circuits.

The first communication interface 2028 can include different implementations depending on which functional units or circuits are being interfaced with the first communication circuit 2016. The first communication interface 2028 can be implemented with technologies and techniques similar to the implementation of the first control interface 2022.

The first interface circuit 2018 allows the user 112 of FIG. 1 to interface and interact with the first device 102. The first interface circuit 2018 can include an input device and an output device. Examples of the input device of the first interface circuit 2018 can include a keypad, a touchpad, soft-keys, a keyboard, a microphone, an infrared sensor for receiving remote signals, or any combination thereof to provide data and communication inputs.

The first interface circuit 2018 can include a first display interface 2030. The first display interface 2030 can include an output device. The first display interface 2030 can include a projector, a video screen, a touch screen, a speaker, a microphone, a keyboard, and combinations thereof.

The first control circuit 2012 can operate the first interface circuit 2018 to display information generated by the compute system 100 and receive input from the user 112. The first control circuit 2012 can also execute the first software 2026 for the other functions of the compute system 100, including receiving location information from the first location circuit 2020. The first control circuit 2012 can further execute the first software 2026 for interaction with the network 104 via the first communication circuit 2016. The first control circuit 2012 can operate the acne diagnostic mechanism 115 of FIG. 1.

The first control circuit 2012 can also receive location information from the first location circuit 2020. The first control circuit 2012 can operate the cancer AI module 118.

The first location circuit 2020 can be implemented in many ways. For example, the first location circuit 2020 can function as at least a part of the global positioning system, an inertial compute system, a cellular-tower location system, a gyroscope, or any combination thereof. Also, for example, the first location circuit 2020 can utilize components such as an accelerometer, gyroscope, or global positioning system (GPS) receiver.

The first location circuit 2020 can include a first location interface 2032. The first location interface 2032 can be used for communication between the first location circuit 2020 and other functional units or circuits in the first device 102.

The first location interface 2032 can receive information from the other functional units/circuits or from external sources, or can transmit information to the other functional units/circuits or to external destinations. The external sources and the external destinations refer to sources and destinations external to the first device 102. The first location interface 2032 can receive the global positioning location from the global positioning system (not shown).

The first location interface 2032 can include different implementations depending on which functional units/circuits or external units/circuits are being interfaced with the first location circuit 2020. The first location interface 2032 can be implemented with technologies and techniques similar to the implementation of the first control circuit 2012.

The second device 106 can be optimized for implementing an embodiment of the present invention in a multiple device embodiment with the first device 102. The second device 106 can provide the additional or higher performance processing power compared to the first device 102. The second device 106 can include a second control circuit 2034, a second communication circuit 2036, a second user interface 2038, and a second storage circuit 2046.

The second user interface 2038 allows an operator (not shown) to interface and interact with the second device 106. The second user interface 2038 can include an input device and an output device. Examples of the input device of the second user interface 2038 can include a keypad, a touchpad, soft-keys, a keyboard, a microphone, or any combination thereof to provide data and communication inputs. Examples of the output device of the second user interface 2038 can include a second display interface 2040. The second display interface 2040 can include a display, a projector, a video screen, a speaker, or any combination thereof.

The second control circuit 2034 can execute a second software 2042 to provide the intelligence of the second device 106 of the compute system 100. The second software 2042 can operate in conjunction with the first software 2026. The second control circuit 2034 can provide additional performance compared to the first control circuit 2012.

The second control circuit 2034 can operate the second user interface 2038 to display information. The second control circuit 2034 can also execute the second software 2042 for the other functions of the compute system 100, including operating the second communication circuit 2036 to communicate with the first device 102 over the network 104.

The second control circuit 2034 can be implemented in a number of different manners. For example, the second control circuit 2034 can be a processor, an embedded processor, a microprocessor, hardware control logic, a hardware finite state machine (FSM), a digital signal processor (DSP), or a combination thereof.

The second control circuit 2034 can include a second control interface 2044. The second control interface 2044 can be used for communication between the second control circuit 2034 and other functional units or circuits in the second device 106. The second control interface 2044 can also be used for communication that is external to the second device 106.

The second control interface 2044 can receive information from the other functional units/circuits or from external sources, or can transmit information to the other functional units/circuits or to external destinations. The external sources and the external destinations refer to sources and destinations external to the second device 106.

The second control interface 2044 can be implemented in different ways and can include different implementations depending on which functional units/circuits or external units/circuits are being interfaced with the second control interface 2044. For example, the second control interface 2044 can be implemented with a pressure sensor, an inertial sensor, a microelectromechanical system (MEMS), optical circuitry, waveguides, wireless circuitry, wireline circuitry, or a combination thereof.

The second storage circuit 2046 can store the second software 2042. The second storage circuit 2046 can also store the information such as data representing incoming images, data representing previously presented image, sound files, or a combination thereof. The second storage circuit 2046 can be sized to provide the additional storage capacity to supplement the first storage circuit 2014.

For illustrative purposes, the second storage circuit 2046 is shown as a single element, although it is understood that the second storage circuit 2046 can be a distribution of storage elements. Also, for illustrative purposes, the compute system 100 is shown with the second storage circuit 2046 as a single hierarchy storage system, although it is understood that the compute system 100 can include the second storage circuit 2046 in a different configuration. For example, the second storage circuit 2046 can be formed with different storage technologies forming a memory hierarchal system including different levels of caching, main memory, rotating media, or off-line storage.

The second storage circuit 2046 can be a controller of a volatile memory, a nonvolatile memory, an internal memory, an external memory, or a combination thereof. For example, the second storage circuit 2046 can be a controller of a nonvolatile storage such as non-volatile random-access memory (NVRAM), Flash memory, disk storage, or a volatile storage such as static random access memory (SRAM).

The second storage interface 2048 can receive information from the other functional units/circuits or from external sources, or can transmit information to the other functional units/circuits or to external destinations. The external sources and the external destinations refer to sources and destinations external to the second device 106.

The second storage interface 2048 can include different implementations depending on which functional units/circuits or external units/circuits are being interfaced with the second storage circuit 2046. The second storage interface 2048 can be implemented with technologies and techniques similar to the implementation of the second control interface 2044.

The second communication circuit 2036 can enable external communication to and from the second device 106. For example, the second communication circuit 2036 can permit the second device 106 to communicate with the first device 102 over the network 104.

The second communication circuit 2036 can also function as a communication hub allowing the second device 106 to function as part of the network 104 and not limited to be an endpoint or terminal unit or circuit to the network 104. The second communication circuit 20 36 can include active and passive components, such as microelectronics or an antenna, for interaction with the network 104.

The second communication circuit 2036 can include a second communication interface 7150. The second communication interface 2050 can be used for communication between the second communication circuit 2036 and other functional units or circuits in the second device 106. The second communication interface 2050 can receive information from the other functional units/circuits or can transmit information to the other functional units or circuits.

The second communication interface 2050 can include different implementations depending on which functional units or circuits are being interfaced with the second communication circuit 2036. The second communication interface 2050 can be implemented with technologies and techniques similar to the implementation of the second control interface 2044.

The second communication circuit 2036 can couple with the network 104 to send information to the first device 102. The first device 102 can receive information in the first communication circuit 2016 from the second device transmission 2010 of the network 104. The compute system 100 can be executed by the first control circuit 2012, the second control circuit 2034, or a combination thereof. For illustrative purposes, the second device 106 is shown with the partition containing the second user interface 2038, the second storage circuit 2046, the second control circuit 2034, and the second communication circuit 2036, although it is understood that the second device 106 can include a different partition. For example, the second software 2042 can be partitioned differently such that some or all of its function can be in the second control circuit 2034 and the second communication circuit 2036. Also, the second device 106 can include other functional units or circuits not shown in FIG. 20 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 100 is described by operation of the first device 102 and the second device 106. It is understood that the first device 102 and the second device 106 can operate any of the modules and functions of the compute system 100.

Figure 21:
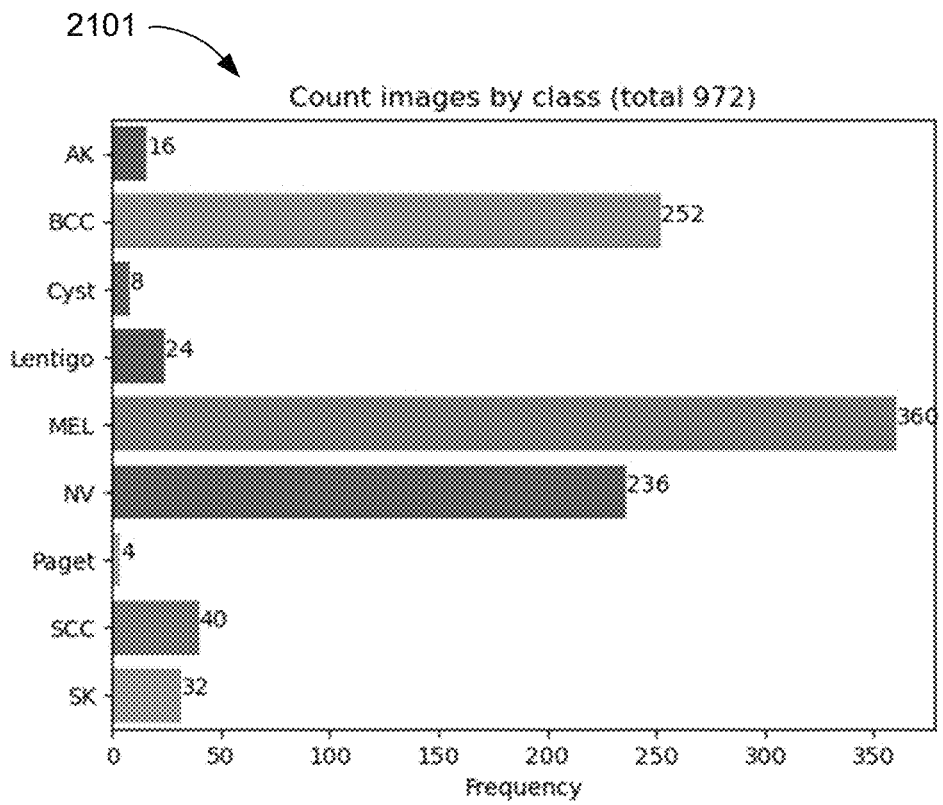
FIG. 21 is an exemplary bar chart of an AUROC curve for the prediction of the cancer AL.

Referring now to FIG. 21, therein is shown an exemplary bar chart 2101 of an AUROC curve for the prediction of the cancer AI 118 of FIG. 1.

Figure 22:
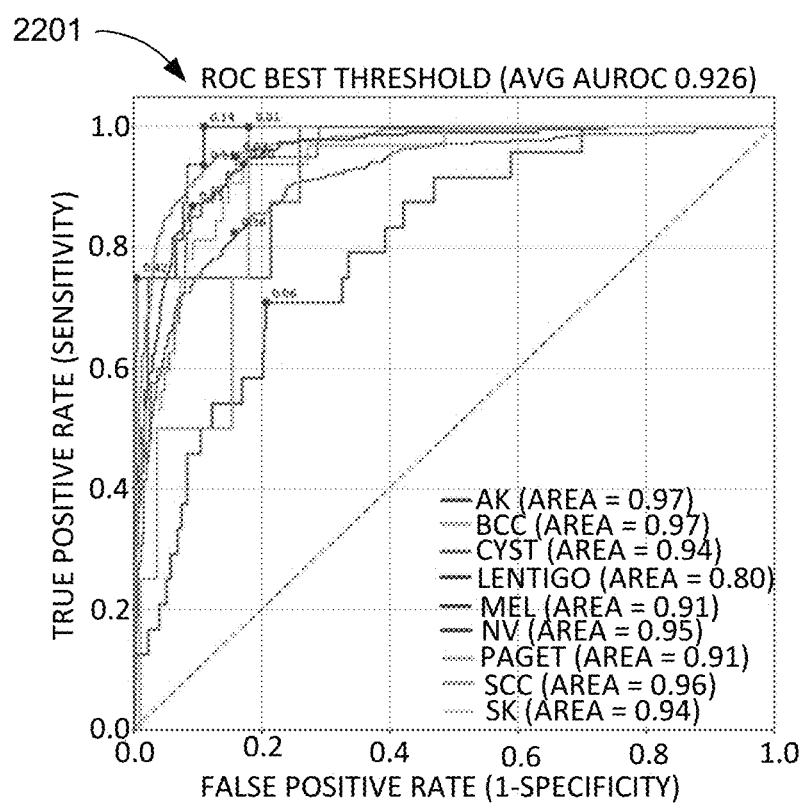
FIG. 22 is an exemplary receiver operating characteristic (ROC) validation curve of sensitivity of the cancer AI.

Referring now to FIG. 22, therein is shown an exemplary receiver operating characteristic (ROC) validation curve 2201 of sensitivity of the cancer AI 118 of FIG. 1.

Figure 23:
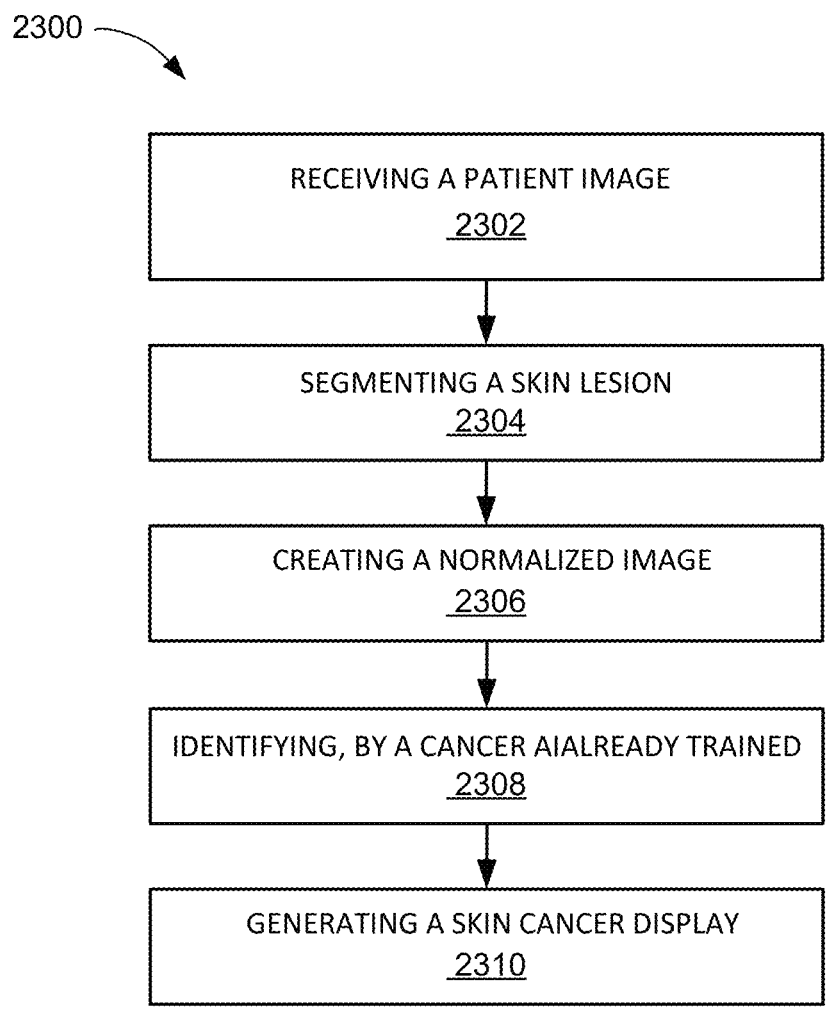
FIG. 23 is a flow chart of a method of operation of a compute system in an embodiment of the present invention.

Referring now to FIG. 23, therein is shown is a flow chart of a method of operation 2300 of a compute system 100 in an embodiment of the present invention. The method 2300 includes: receiving a patient image in a block 2302; segmenting a skin lesion in the patient image in a block 2304; constructing a normalized image by cropping the patient image and adding padding to position the skin lesion at the center of the normalized image in a block 2306; identifying, by a cancer artificial intelligence (AI) already trained, a skin cancer classification, a skin cancer sub-class, and a risk level assessment in a block 2308; and generating a skin cancer display including the normalized image, the skin cancer classification, the skin cancer sub-class, and the risk level assessment for displaying on a device in a block 2310.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
    receiving a patient image;
    segmenting a skin lesion in the patient image;
    constructing a normalized image by cropping the patient image and adding padding to position the skin lesion at a center of the normalized image;
    identifying, by a cancer artificial intelligence (AI) already trained, a skin cancer classification, a skin cancer sub-class, and a risk level assessment; and
    generating a skin cancer display including the normalized image, the skin cancer classification, the skin cancer sub-class, and the risk level assessment for displaying on a device.

2. The method as claimed in claim 1 wherein identifying the skin cancer sub-class includes submitting a class prediction and a sub-class prediction to a multiplier for calculating the skin cancer sub-class.

3. The method as claimed in claim 1 wherein identifying the skin cancer classification includes identifying Melanoma (MEL), Basal Cell Carcinoma (BCC), Epidermal tumors (EPI), Malignant lesions (MALO), Melanocytic Nevus (NV), Dermatofibroma (DF), Benign Adnexal Lesions (BAL), Benign Keratinocytic Lesions (BKL), Benign Vascular lesions (VASC), or Benign Lesions (BENO).

4. The method as claimed in claim 1 wherein identifying the risk level assessment by the cancer AI includes identifying a risk level zero through a risk level five.

5. The method as claimed in claim 1 wherein the cancer artificial intelligence (AI) already trained includes the cancer artificial intelligence (AI) detecting the skin cancer classification and the skin cancer sub-class for displaying on the skin cancer display.

6. The method as claimed in claim 1 wherein generating the skin cancer display includes identifying the risk level assessment as the risk level zero indicating low risk through the risk level five indicating high risk.

7. The method as claimed in claim 1 further comprising screening the patient image to identify an oops score between 0.75 and 0.25 as an input to the normalized image.

8. A compute system comprising:
    a control circuit, including a processor, configured to:
        receive a patient image;
        segment a skin lesion in the patient image;
        construct a normalized image by cropping the patient image and adding padding to position the skin lesion at the center of the normalized image;
        identify, by a cancer artificial intelligence (AI) already trained, a skin cancer classification, a skin cancer sub-class, and a risk level assessment; and
        generate a skin cancer display including the normalized image, the skin cancer classification, the skin cancer sub-class, and the risk level assessment for displaying on a device.

9. The system as claimed in claim 8 wherein identifying the skin cancer sub-class includes submitting a class prediction and a sub-class prediction to a multiplier for calculating the skin cancer sub.

10. The system as claimed in claim 8 wherein identifying the skin cancer classification includes identifying Melanoma (MEL), Basal Cell Carcinoma (BCC), Epidermal tumors (EPI), Malignant lesions (MALO), Melanocytic Nevus (NV), Dermatofibroma (DF), Benign Adnexal Lesions (BAL), Benign Keratinocytic Lesions (BKL), Benign Vascular lesions (VASC), or Benign Lesions (BENO).

11. The system as claimed in claim 8 wherein identifying the risk level assessment by the cancer AI includes identifying a risk level zero through a risk level five.

12. The system as claimed in claim 8 wherein the cancer artificial intelligence (AI) already trained includes the cancer artificial intelligence (AI) configured to detect the skin cancer classification and the skin cancer sub-class for displaying on the skin cancer display.

13. The system as claimed in claim 8 wherein the skin cancer display generated includes the risk level assessment identified as the risk level zero indicating low risk through the risk level five indicating high risk.

14. The system as claimed in claim 8 further comprising screen the patient image to identify an oops score between 0.75 and 0.25 as an input to the normalized image.

15. A non-transitory computer readable medium including instructions for a compute system comprising:
- receiving a patient image;
- segmenting a skin lesion in the patient image;
- constructing a normalized image by cropping the patient image and adding padding to position the skin lesion at the center of the normalized image;
- identifying, by a cancer artificial intelligence (AI) already trained, a skin cancer classification, a skin cancer sub-class, and a risk level assessment; and
- generating a skin cancer display including the normalized image, the skin cancer classification, the skin cancer sub-class, and the risk level assessment for displaying on a device.

16. The non-transitory computer readable medium as claimed in claim 15 wherein identifying the skin cancer sub-class includes submitting a class prediction and a sub-class prediction to a multiplier for calculating the skin cancer sub-class.

17. The non-transitory computer readable medium as claimed in claim 15 wherein identifying the skin cancer classification includes identifying Melanoma (MEL), Basal Cell Carcinoma (BCC), Epidermal tumors (EPI), Malignant lesions (MALO), Melanocytic Nevus (NV), Dermatofibroma (DF), Benign Adnexal Lesions (BAL), Benign Keratinocytic Lesions (BKL), Benign Vascular lesions (VASC), or Benign Lesions (BENO).

18. The non-transitory computer readable medium as claimed in claim 15 wherein identifying the risk level assessment by the cancer AI includes identifying a risk level zero through a risk level five.

19. The non-transitory computer readable medium as claimed in claim 15 wherein the cancer artificial intelligence (AI) already trained includes the cancer artificial intelligence (AI) detecting the skin cancer classification and the skin cancer sub-class for displaying on the skin cancer display.

20. The non-transitory computer readable medium as claimed in claim 15 wherein generating the skin cancer display includes identifying the risk level assessment as the risk level zero indicating low risk through the risk level five indicating high risk.

* * * * *